United States Patent
Nagpal et al.

(10) Patent No.: US 11,473,135 B2
(45) Date of Patent: Oct. 18, 2022

(54) HIGH-THROUGHPUT BLOCK OPTICAL DNA SEQUENCE IDENTIFICATION

(71) Applicant: The Regents of the University of Colorado, Denver, CO (US)

(72) Inventors: Prashant Nagpal, Lafayette, CO (US); Manjunatha Sagar Dodderi, Dayton, MN (US)

(73) Assignee: THE REGENTS OF THE UNIVERSITY OF COLORADO, A BODY CORPORATE, Denver, CO (US)

( * ) Notice: Subject to any disclaimer, the term of this patent is extended or adjusted under 35 U.S.C. 154(b) by 700 days.

(21) Appl. No.: 16/211,817

(22) Filed: Dec. 6, 2018

(65) Prior Publication Data

US 2020/0299762 A1    Sep. 24, 2020

Related U.S. Application Data

(60) Provisional application No. 62/595,551, filed on Dec. 6, 2017.

(51) Int. Cl.
*C12Q 1/6869* (2018.01)
*G01N 21/65* (2006.01)

(52) U.S. Cl.
CPC ......... *C12Q 1/6869* (2013.01); *G01N 21/658* (2013.01); *C12Q 2565/632* (2013.01)

(58) Field of Classification Search
CPC ............ C12Q 1/6816; C12Q 2565/632; C12Q 2563/155; C12Q 1/6869; C12Q 1/632; B82Y 15/00; B82Y 5/00; G01N 21/658
See application file for complete search history.

(56) References Cited

U.S. PATENT DOCUMENTS

| 6,284,465 B1 * | 9/2001 | Wolber | G01N 21/253 250/559.29 |
| 2004/0023293 A1 * | 2/2004 | Kreimer | F28D 15/02 506/6 |

(Continued)

FOREIGN PATENT DOCUMENTS

WO   WO-2017176679 A1 * 10/2017 ............... C12Q 1/68

*Primary Examiner* — Sang H Nguyen
(74) *Attorney, Agent, or Firm* — Berg Hill Greenleaf Ruscitti LLP

(57) ABSTRACT

Disclosed herein is a multiplexed design with three-dimensional plasmonic nanofocusing and confinement of light, demonstration of reproducible and robust single-molecule optical fingerprints using two complementary vibrational spectroscopy techniques (infrared and Raman spectroscopy), identification of respective vibrational modes which uniquely fingerprint the biomolecular species, and facile differentiation of respective fingerprints in DNA mixtures, as well as epigenetic modifications. While the nanometer scale mode volumes still prevent single letter identification of DNA sequence, we show an alternative method for identifying A, T, G, C DNA nucleotides in "k-mers" using sequences of these blocks as a unique and high-throughput alternative to single letter sequences (similar to binary and hexadecimal systems). Furthermore, additivity shown in single-molecule DNA mixtures and robust optical signatures can also be used in a raster-type step scan to identify single letter sequences. These results can pave the way for the development of a novel, high-throughput block optical sequencing (BOS) method.

10 Claims, 15 Drawing Sheets

Specification includes a Sequence Listing.

(56) References Cited

U.S. PATENT DOCUMENTS

| | | | |
|---|---|---|---|
| 2007/0048746 A1* | 3/2007 | Su | G01N 33/54366 435/6.11 |
| 2007/0247620 A1* | 10/2007 | Koo | G01N 21/658 356/301 |
| 2008/0241569 A1* | 10/2008 | Qin | B82Y 30/00 428/548 |
| 2016/0024570 A1* | 1/2016 | Ju | C12Q 1/6874 435/6.11 |
| 2017/0299601 A1* | 10/2017 | Giraldo Gomez | G01N 21/6489 |
| 2017/0335376 A1* | 11/2017 | Ivarez Puebla | B82Y 15/00 |

* cited by examiner

HIGH-THROUGHPUT BLOCK OPTICAL DNA SEQUENCE IDENTIFICATION

CROSS-REFERENCE TO RELATED APPLICATIONS

This application claims benefit of priority pursuant to 35 U.S.C. § 119(e) of U.S. provisional patent application No. 62/595,551 entitled "HIGH-THROUGHPUT BLOCK OPTICAL DNA SEQUENCE IDENTIFICATION," filed on Dec. 6, 2017, which is hereby incorporated by reference in its entirety.

FIELD

The disclosed compositions, devices, processes, methods, and systems are directed to rapid and accurate optical fingerprinting, identification, and sequencing of nucleic acid polymers.

SEQUENCE LISTING

A sequence listing submitted in computer readable format is hereby incorporated by reference. The computer readable file is named P270121us02_ST25.txt, created Dec. 5, 2018 and is 4 KB in size.

BACKGROUND

Optical techniques for molecular diagnostics or DNA sequence identification generally rely on small molecule fluorescent labels, which utilize light with a wavelength of several hundred nanometers for detection. Developing a label-free optical DNA sequencing technique will require focusing of light toward single molecules, a high-throughput and multiplexed identification method, and a data compression technique to rapidly identify sequences while extracting useful information about genomic heterogeneity for big datasets.

DNA sequencing of single-molecules can provide vital information about genetic heterogeneity and its role in defining biological functions by controlling the downstream expression of genes, proteins, and other cell-regulatory processes. Small variations in genetic coding across individual cells, both through mutations or epigenetic influences, play a key role in physiology and provide new targets for diagnostics, vaccine development, and therapeutics. To realize the benefits of single-molecule sequencing, several fundamental elements of the technology must be further developed. Improvements would result from high-throughput and multiplexed data acquisition, data compression to rapidly extract useful information from large sets of raw sequence data, and a novel platform that does not rely on expensive labels or sample preparation. Optical sequencing of DNA might be useful in addressing these elements, but would require parallel optics and data acquisition, multiplexed label-free probes, and inexpensive processing steps. However, light photons have several hundred nanometer wavelengths, which is much greater than the molecular length-scales needed to identify a single nucleotide, photon interactions with single-molecules must be measured using optical spectroscopy, and multiplexed parallel probes must be developed for simultaneous reading. Only then could characterization of optical measurements be used for DNA sequence identification. Storing and analyzing massive amounts of sequence data can also create potential issues. For example, storing single DNA nucleotide letters (adenine (A), guanine (G), cytosine (C), and thymine (T)) for a nominal human genome requires several gigabytes of space per sequence, so 100 DNA sequences need terabytes of space and data mining to extract useful information. Similarly, a few thousand bacterial genomes to map the microbiome would require similar space and data processing. To remedy this, data compression techniques use lossless and lossy compression.

Described herein is the use of Raman spectroscopy and FTIR spectroscopy for label-free identification of DNA nucleobases. The disclosed method identifies characteristic molecular vibrations using optical spectroscopy, especially using the "fingerprinting region" for different molecules from ~400-1400 $cm^{-1}$, to determine the nucleotide content of a block, or portion, of a polynucleotide. These block fingerprints can then be analyzed and compared with other block fingerprints to identify a specific target polynucleotide or genetic sequence.

SUMMARY

Disclosed herein are devices, methods, and systems for rapid and high throughput sequencing of DNA using optical methods to identify the nucleotide content of a block of a polynucleotide. The disclosed methods may include an inherent lossy compression of genomic information, which can be used to rapidly identify specific target sequences, epigenetic modifications, mutations, polymorphisms, insertions, and deletions, as well as provide genetic sequence information. In one embodiment, the disclosed methods and systems combine Raman spectroscopy with other optical methods, such as FTIR to help increase the sensitivity and accuracy of fingerprinting as well as sequencing.

BRIEF DESCRIPTION OF THE DRAWINGS

FIG. 1, Panel a) SEM image of nanopyramids (left) and a schematic of DNA molecules on the nanopyramid tips (center) for block optical sequencing. Additivity of signal from k-mer blocks of nucleotides allows for block optical DNA sequencing. FIG. 1, Panel b) Surface-enhanced Raman signal for benzenethiol molecules on silver nanopyramid tips. FIG. 1, Panel c) Surface-enhanced Raman signal for adenine k-mers on nanopyramid tips. Raman signal of adenine on nanopyramids is much stronger than a tenfold higher concentration of adenine on a flat silver surface. FIG. 1, Panels d and e) IR and visible extinction spectra for surface plasmon resonance of the nanopyramids. The position of the Raman excitation laser is marked at 632.8 nm. Uniform Raman enhancement of all modes was attributed to the broad plasmon enhancement around the Raman excitation laser (for both Stokes and anti-Stokes scattering), whereas several plasmon peaks in the IR region correspond well with selective (or plasmon enhancement) of respective IR vibrational peaks. FIG. 1, Panel f) Normalized integrated area for a single Raman peak in the spectra for dATP as the molar ratio of a glycine contaminant increases. FIG. 1, Panel g) Direct comparison of Raman spectra from pure dATP and equimolar glycine and dATP, indicating that the presence of biomolecule contaminants does not significantly affect Raman signal from DNA nucleotides. Dashes in the spectra indicate where the low- and high-shift regions were spliced together. These spectra were collected on a flat glass substrate, and therefore do not show the same Raman enhanced peaks seen for adenine k-mers on the silver nanopyramid substrate.

FIG. 2, Panel a) adenine, FIG. 2, Panel b) thymine, FIG. 2, Panel c) cytosine, and FIG. 2, Panel d) guanine. The strong modes are marked in uppercase letters, while the weak modes are in lowercase letters. The corresponding chemical structures show the specific vibrations (bond bending shown using arrows, bond stretching and ring breathing shown using double arrows) associated with numbered peaks for respective nucleobases. FIG. 2, Panel e) Raman spectra for a DNA oligomer of repeating ATGC, poly(dATGC)$_4$. Peaks from all nucleobases can be seen contributing to the overall signal.

FIG. 3, Panel a) Fitting and characterizing homologous block k-mer spectra peaks for use as fingerprints for base calling. Using adenine Raman spectra as an example (shown on the left), we fit Gaussians to all characteristic peaks, allowing us to determine the center location and corresponding FWHM for each. Only the most unique peaks (shown with an x in the tables on the right for both Raman and FTIR) were used in the base calling analysis as fingerprints for homologous sequences. To identify unknown spectra obtained from Raman and FTIR measurements, the spectra are compared with the fingerprints in terms of the area under the respective fingerprinting peaks. For Raman data, this represents the total number of scattered photons by the specific mode. FIG. 3, Panel b) All major spectra peaks are used for base calling mixed k-mer blocks. As shown for thymine, single peaks do not show consistent trends (left); however, when combined the trends become favorable for fractional identification (right). FIG. 3, Panel c) Calibration curves used to deduce the relative fraction of each nucleobase in a mixed sequence k-mer. Only three (A, C, and T) calibration curves are needed, as the fourth (G) can be found from the remainder. FIG. 3, Panel d) Probability values (obtained from the base calling algorithm), the confidence of base calling, and accuracy (X indicates incorrect calls) using only Raman spectra to identify homologous k-mer blocks of each nucleobase (SEQ ID NO:20). FIG. 3, Panel e) Improved confidence and accuracy in base calling homologous k-mer blocks can be seen by combining Raman and FTIR spectra (SEQ ID NO:21). FIG. 3, Panel f) Summary of base calling accuracy for 396 measured homologous k-mer block spectra (99 each for A, T, G, and C) using combined Raman and FTIR spectroscopy. FIG. 3, Panel g) High accuracy for identifying nucleobases in various mixed sequence k-mer blocks.

DETAILED DESCRIPTION

Figure 1:
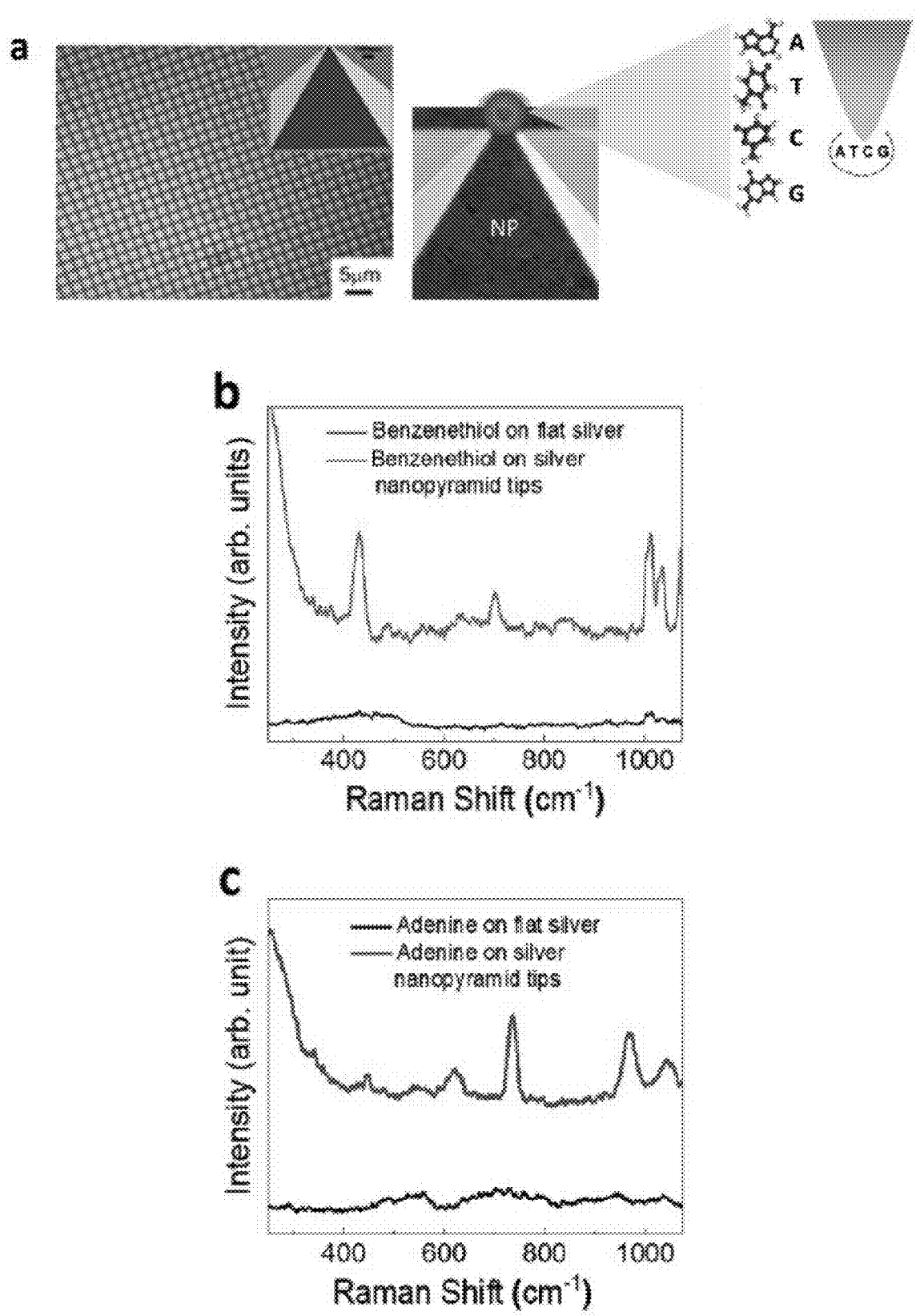
FIG. 1, Panels a-g, shows the design of multiplexed nanopyramid probes for robust optical DNA sequencing.
Figure 1:
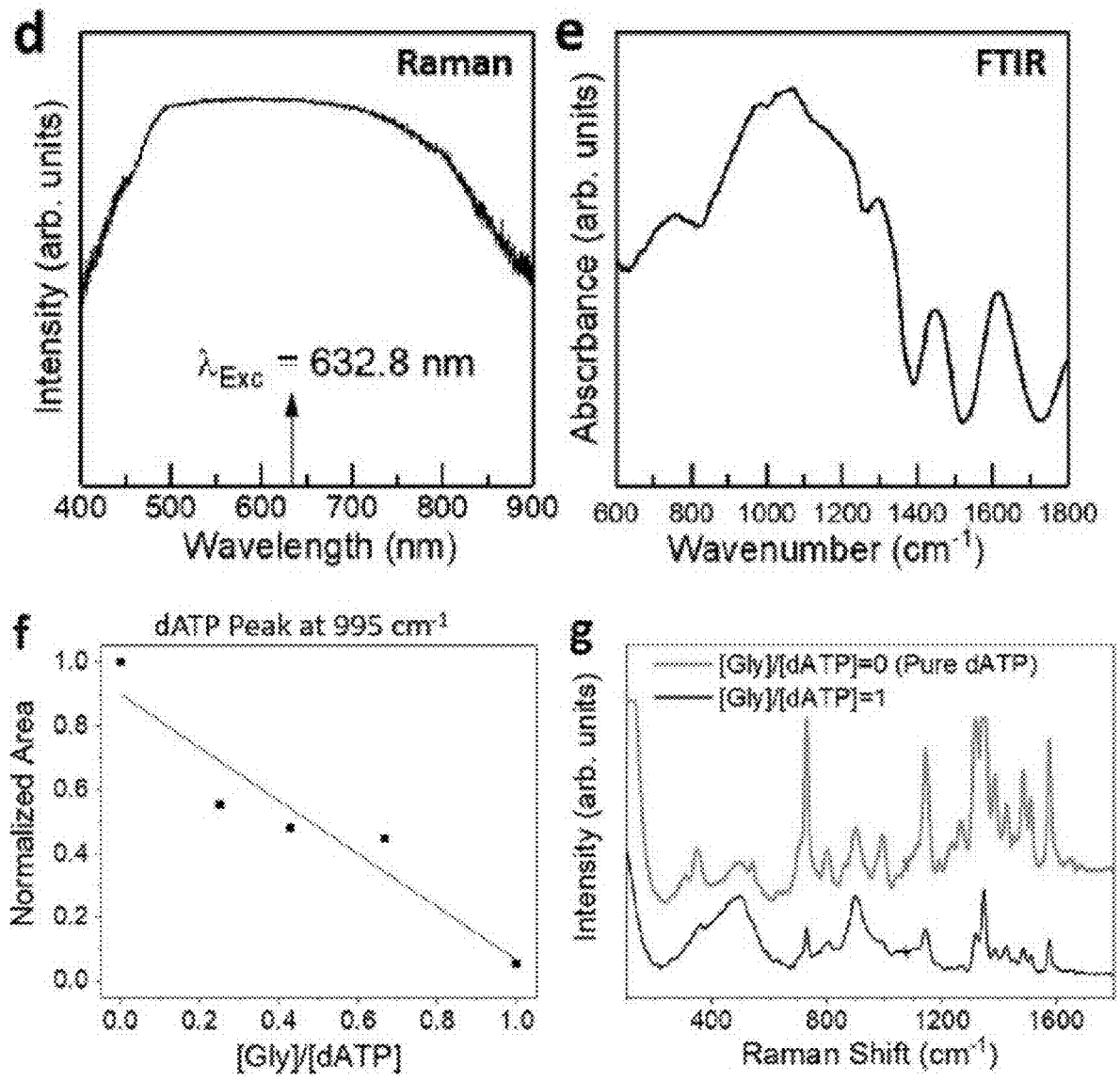

Described herein are devices, techniques, and systems that employ multiplexed 3D plasmonic nanofocusing, optical signatures from nanometer-scale mode volumes to aid in identifying A, T, G, and C content in DNA k-mer blocks. The content of each nucleotide in a block can be used as a unique and high-throughput method for identifying sequences, genes, and other biomarkers as an alternative to single-letter sequencing.

Here, surface-enhanced Raman spectroscopy is used for label-free identification of DNA nucleobases with multiplexed 3D plasmonic nanofocusing. While nanometer-scale mode volumes may prevent the identification of single nucleobases within a DNA sequence, the block optical technique is shown to be useful to identify A, T, G, and C content in DNA k-mers. It is shown that the content of each nucleotide in a DNA block can be used as a unique and high-throughput method for identifying sequences, genes, and other biomarkers as an alternative to single letter sequencing. Additionally, it is shown that coupling two complementary vibrational spectroscopy techniques (infrared and Raman spectroscopy) can improve block characterization. These results can pave the way for the development of a novel, high-throughput block optical sequencing method with lossy genomic data compression using k-mer identification from multiplexed optical data acquisition.

The described devices, processes, and systems are useful in label-free, high-throughput block optical sequencing (BOS) with inherent lossy compression. In many of these embodiments, k-mer blocks of DNA are read using 3D nanofocusing of light.

Since the different nucleobases in DNA are biochemically distinct, their unique interactions with light photons (observable optical fingerprints) can be used to discriminate them. Surface-enhanced Raman spectroscopy (SERS) is an optical method routinely used for identification of unknown chemical and biochemical compounds from their vibrational fingerprints. In this technique, surface plasmon polaritons lead to 3D nanofocusing and enhancement of near field signal at the apex of rough features or patterned nanostructures However, applying SERS, or the related tip-enhanced Raman spectroscopy (TERS), for reproducible single-molecule DNA sequence identification has proven difficult.

Previous studies have used SERS/TERS measurements on DNA for label-free chemical fingerprinting; however, mixing of a large number of DNA molecules with metal nanoparticles provides an ensemble spectra and poses uncertainties in signal strengths. Furthermore, DNA molecules have varied enhancement due to differences in their location from the plasmonic antenna, and thus suffer from low reproducibility. Since the SERS/TERS signal falls off dramatically with distance from the plasmonic antenna, it makes signal amplitudes highly sensitive to the orientation and conformation of molecules with respect to the surface. While many of these effects are washed out in an ensemble detection, it has been shown that the SERS/TERS signal strength and reproducibility are severely affected by the packing fraction and large uncontrollable variation in molecular orientation with respect to the plasmonic nanostructure. Thus, single-molecule label-free identification of DNA nucleobases remains an important and critical challenge.

Described herein is the use of patterned nanopyramid probes on a multiplexed substrate to reproducibly enhance "optical fingerprints" of DNA nucleotides. Identifying the different molecular vibrations, bond stretches, and rocking motions in these reproducible spectra allowed differentiation of the nucleobases from their respective spectral fingerprints. In addition, the disclosed identification techniques may be improved by combining Raman with Fourier-transform infrared (FTIR) spectroscopy.

Probes

Probes for use with the disclosed methods and techniques may be fabricated using methods known to those of skill in the art to obtain a suitable shape for providing Raman scatter or FTIR absorbance information from a polynucleotide. In some embodiments, the probes may be manufactured with a pyramidal shape of three or four sides, such that they end in a tip with significantly reduced surface area relative the base of the shape. In other embodiments, the shape may be other than pyramidal, for example square, conical, or cylindrical.

In many embodiments, nanopyramidal probes may be fabricated from various compositions. In some embodiments, metal pyramids are used. In one embodiment, the periodicity of the nanopyramids may be about 2 $\mu m$ and in various suitable patterns. For example, as described below, a square periodic pattern may be used with 2 $\mu m$ periodicity in both the x and y direction (see FIG. 1, Panel a, and FIG. 4). In many embodiments, this may help enhance vibrational signal using the fingerprinting region of the mid-IR region.

Probes may have characteristics that help to retain a polynucleotide at the tip. In some embodiments, the composition of the material at the tip of the probe may have a charge that is opposite of the polynucleotide to aid in retaining the polynucleotide, for example the tip may be positively charged to attract and retain negatively charged polynucleotides. In some embodiments, other surfaces of the tip may be of a material that may repel or poorly interact with a polynucleotide.

Probes for use with the disclosed methods and techniques may define a surface for accepting or interrogating a polynucleotide. In some embodiments, the surface of the probe may be a tip of the probe that may be blunt or sharp. A blunt tip may define a surface that can accommodate a polynucleotide of 1 to about 10 nm. In many embodiments, the polynucleotide being interrogated may be longer than the surface of the tip. In some embodiments, the tip may have a have a diameter of about 1 to 10 nm, or about 2-7 nm, or about 2 nm, 3 nm, 4 nm, or 5 nm. In many embodiments, the tip may be designed to interrogate a portion or block of a polynucleotide that is from about 2 to about 20 nt. In other embodiments, the tip may be designed to interrogate 3 nt to about 10 nt.

A surface for use with the disclosed devices, methods, techniques, and systems may have a plurality of probes. In some embodiments, a surface may have about $1\times10^5$ to about $1\times10^{10}$ probes, for example $1\times10^6$ or $1\times10^9$ probes. In many embodiments, a plurality of probes may be analyzed simultaneously or sequentially for Raman scatter and FTIR for the nucleotide content of a polynucleotide positioned on the tip of the probe.

Spectroscopy

Laser light may be directed at one or more probes to interrogate a polynucleotide at, on, or near a tip of the probe. In many embodiments, the laser light may have a wavelength of about 600 nm to about 700 nm. In some embodiments, the wavelength may be about 630 nm, or about 632.8 nm.

Light reflected from the portion of the polynucleotide at the tip may be analyzed by various spectrophotometric methods. In some embodiments, scattered light is analyzed by a Raman spectrophotometer. In some embodiments, absorbance may be analyzed by FTIR spectrophotometer. In many embodiments, light from about 100 to about 1800 wavenumber is analyzed. In many embodiments, the analyzed light is from about 400 to about 1400 wavenumber. In some embodiments, one or more filters may be used to analyze light within the wavenumber range.

Preparation of Nucleic Acids

Polynucleotides for use with the disclosed methods and techniques may be prepared by various methods known to those of skill in the art. In some embodiments, the polynucleotides may be deoxy- or ribonucleic acids. In some embodiments, the polynucleotides may be comprised of one or more nucleobases selected from adenine, cytosine, guanine, thymine, and uracil. In some embodiments one or more of the nucleobases may include a methyl group, for example 5-methylcytosine or, in RNA, N6-methyladenosine.

The polynucleotides may be applied to the surface, for example the probe tip by various methods. In most embodiments, wherein the portion of the polynucleotide is interrogated on a probe tip, the tip may support or be in contact with a single polynucleotide. In some embodiments, the polynucleotide may be combed on the surface so that it is substantially linear.

The polynucleotide may be treated prior to applying it to the surface. In one embodiment the polynucleotide is digested or fragmented by enzyme or chemical treatment, for example with a specific DNA nuclease. In some embodiments, the fragmentation may provide a fragment size that is similar to, but generally larger, than that of the block size being analyzed.

Blocks

A portion, or block, of a polynucleotide may be analyzed by the described method. In some embodiments, the block may comprise from about 2 to about 20 nucleotides, for example 2, 3, 4, 5, 6, 7, 8, 9, 10, 11, 12, 13, 14, 15, 16, 17, 18, 19, or 20 nucleotides. The number of nucleotides in a block may be referred to as the "k" number. In most embodiments, a polynucleotide comprises a plurality of blocks.

Fingerprints

The disclosed methods, techniques, devices, and systems are useful in determining the nucleotide composition of an interrogated block. In some embodiments, the disclosed methods may be useful in determining the relative or absolute number of each type of nucleotide in a block. In many embodiments, this composition of a given block may represent a fingerprint for that block.

Lossy

The disclosed methods and techniques for identification and sequencing of polynucleotides may represent lossy compression. In the disclosed techniques and methods, the identity and order of nucleotides within a given block is not determinable by analysis of the light from that tip. In some embodiments, fingerprints of multiple blocks at multiple tips may be combined to provide an overall sequence of a given polynucleotide comprised of the analyzed blocks.

Rastering

The disclosed devices, methods, techniques, and systems may be used to sequence a plurality of polynucleotides by movement of the probe tip relative to the polynucleotide. In this embodiment, the polynucleotide may be applied to a surface other than a probe tip, and then a probe tip may be moved into proximity with the polynucleotide. When the tip is moved along the polynucleotide, the fingerprint will change as one nucleotide at the end of the block is lost, and a new nucleotide is added to the beginning of the block.

The disclosed algorithms, methods, techniques, and systems may be implemented in a digital computer system. Such a digital computer is well-known in the art and may include one or more of a central processing unit, one or more of memory and/or storage, one or more input devices, one or more output devices, one or more communications interfaces, and a data bus. In some embodiments, the memory may be RAM, ROM, hard disk, optical drives, removable drives, etc. In some embodiments, storage may also be included in the disclosed system. In some embodiments, storage may resemble memory that may be remotely integrated into the system. The input and output devices may be, for example one or more monitors, display units, video hardware, printers, speakers, lasers, spectrophotometers, filters, collectors, cameras, etc.

EXAMPLES

Figure 4:
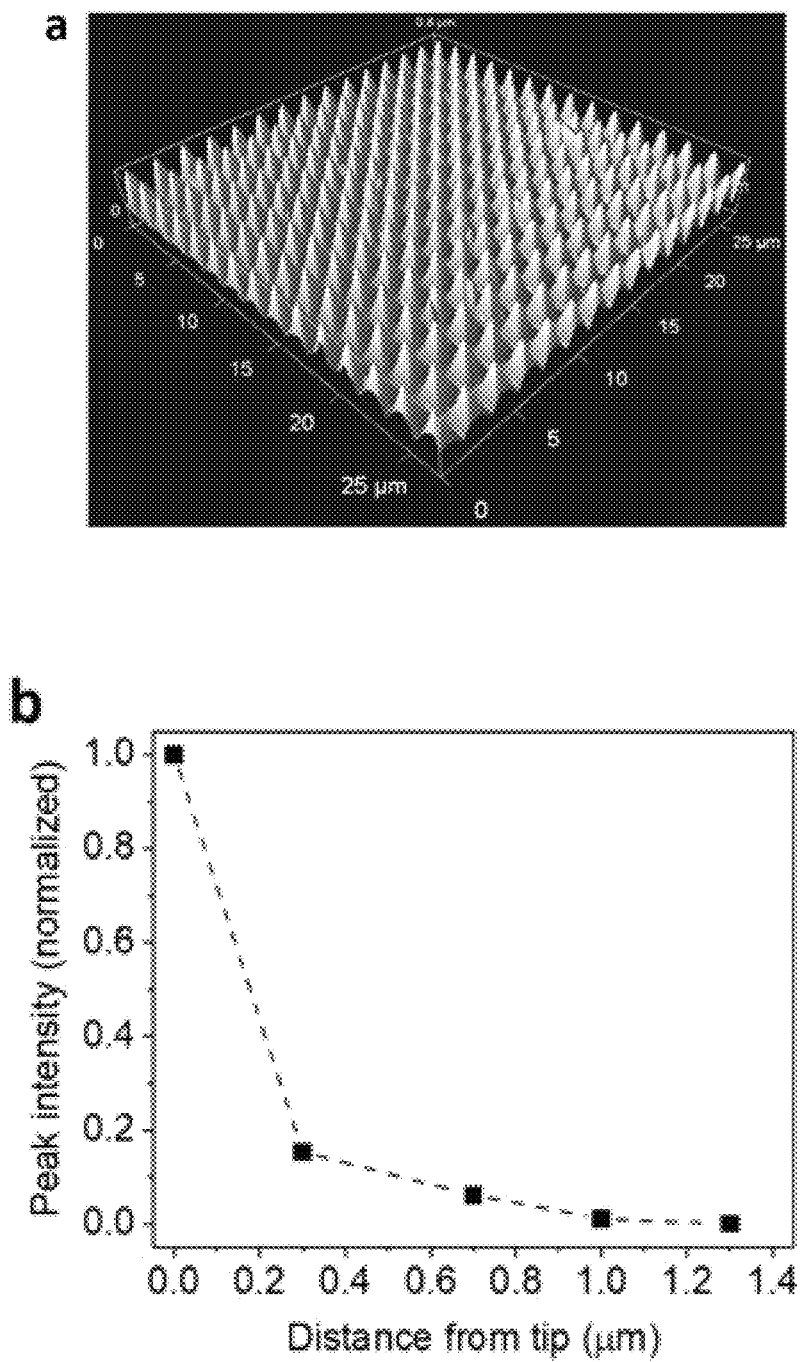
FIG. 4 shows multiplexed nanopyramid optical substrate and signal enhancement. (Panel a) AFM image of the multiplexed optical reader with the designed nanopyramid substrate. (Panel b) Multiphoton confocal cross-sectional variation of amplitude of the Raman spectra for nanopyramids (signal from adenine) vs. distance from the apex of the tip. More than one million tips were present in each multiplexed optical reader used in the study.

A substrate with metal pyramids at 2 µm periodicity (square periodic pattern, 2 µm in both x and y direction, FIG. 1, Panel a; FIG. 4, Supporting Information) was designed to enhance vibrational signal using the fingerprinting region of the mid-IR region. FIG. 4 shows confocal spectra signal from this embodiment of the tips with pixel-limited resolution. To confirm the resolution of our nanopyramid tips, we collected Raman spectroscopy measurements on a self-assembled monolayer of benzenethiol with and without nanopyramids (FIG. 1, Panel b). Previous studies have demonstrated the signal enhancement can be on the order of $10^7$-$10^{10}$. Furthermore, we dropcasted homologous adenine oligomers on nanopyramids at low concentrations ($10 \times 10^{-9}$ to $100 \times 10^{-9}$ m) and compared the Raman spectra with a ten-fold higher concentration on flat silver (FIG. 1, Panel c), which also showed significant signal enhancement. While focusing on Raman spectroscopy, we demonstrate that coupled FTIR spectroscopy can help increase nucleobase identification.

Each of these vibrational spectroscopy techniques shows distinct peaks from four DNA nucleotides and may be useful in characterizing different properties. Raman and FTIR spectra, which may be used to characterize the change in bond polarizability and polarization (or dipole moment) with bond vibrations, respectively, are complementary, have different selection rules, differ in intensity even for the same bond vibrations, and are affected by symmetry and orientation of the single molecules probed. As seen in the plasmon peaks for Raman spectroscopy (FIG. 1, Panel d) and FTIR spectroscopy (mid-IR region, FIG. 1, Panel e), the designed metal nanostructures lead to broadband enhancement of probed vibrational spectra as optical fingerprints. An important consideration when dealing with biological samples is possible contamination from the abundance of biomolecules in the cellular environment. Most notably, the presence of protein contaminants prevents DNA sequence identification from current sequencing methods. To test the extent at which biomolecule contaminants disrupt the optical spectra from DNA, we collected Raman spectra on deoxyadenosine triphosphate (dATP) nucleotides mixed with glycine up to equimolar concentrations. As the ratio of glycine to nucleotides increased, the peak intensities (measured by integrated area under the curve) decreased, but were never extinguished. FIG. 1, Panel f shows the normalized area versus the glycine-dATP molar ratio for a representative adenine peak around 995 $cm^{-1}$. A direct comparison of the full Raman spectra for pure dATP and for equimolar glycine and dATP is given in FIG. 1, Panel g. This provides evidence that the optical vibrational spectroscopic techniques are robust, with signal remaining strong up to significant levels of contamination, in this case glycine.

Figure 2:
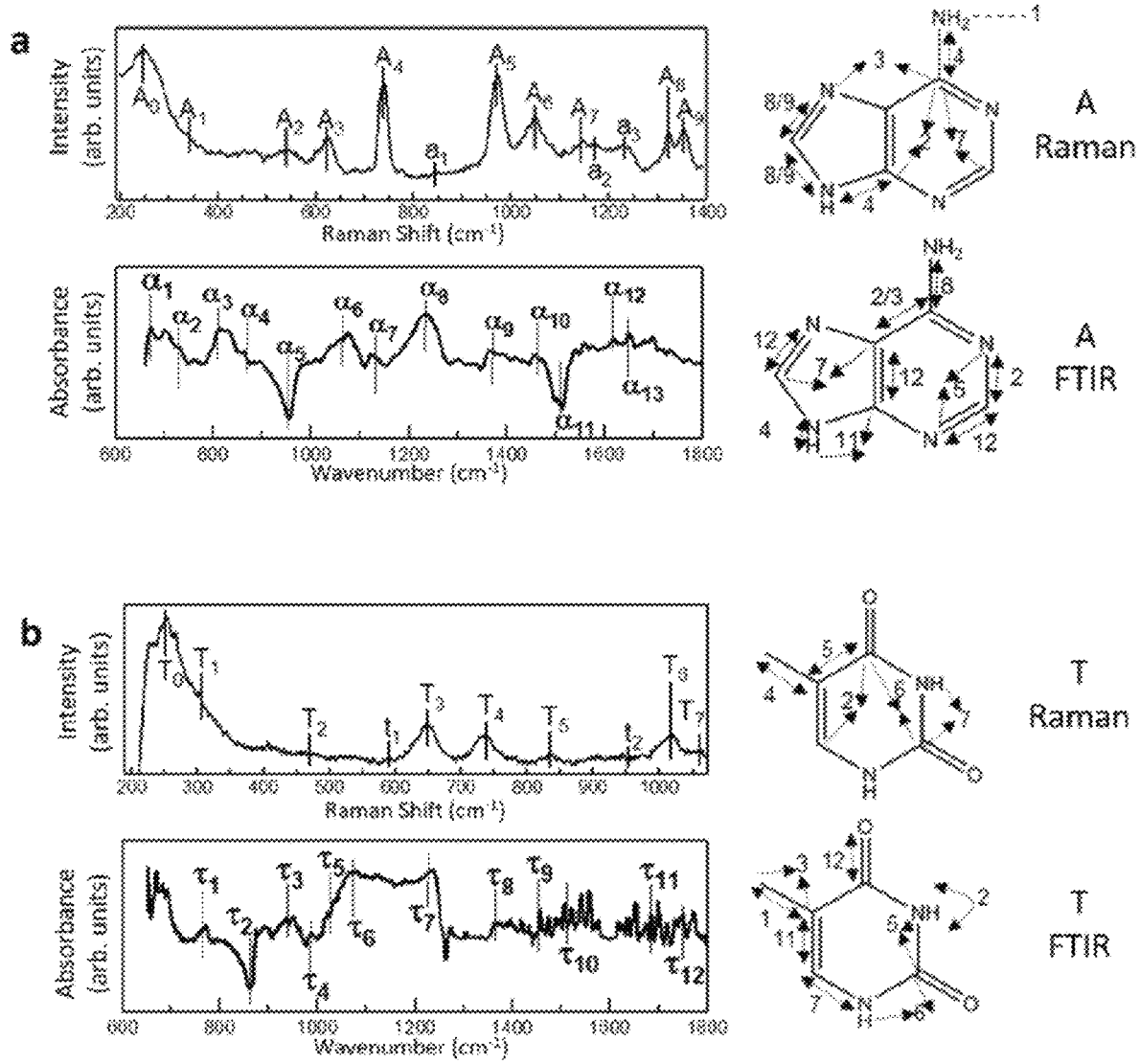
FIG. 2, Panels a-e shows the identification of Raman and FT R peaks as optical fingerprints for DNA nucleobases.
Figure 2:
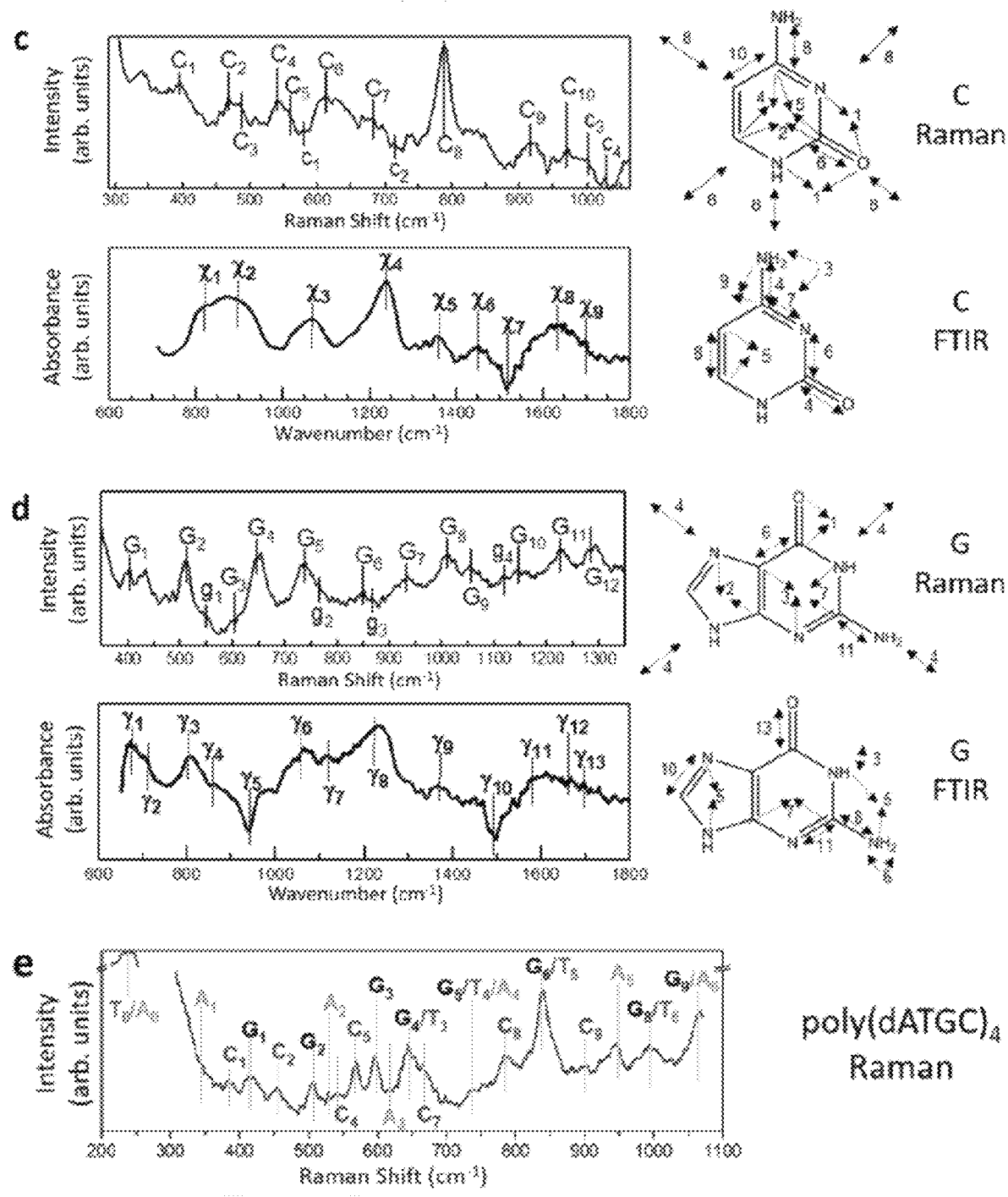
Figure 5:
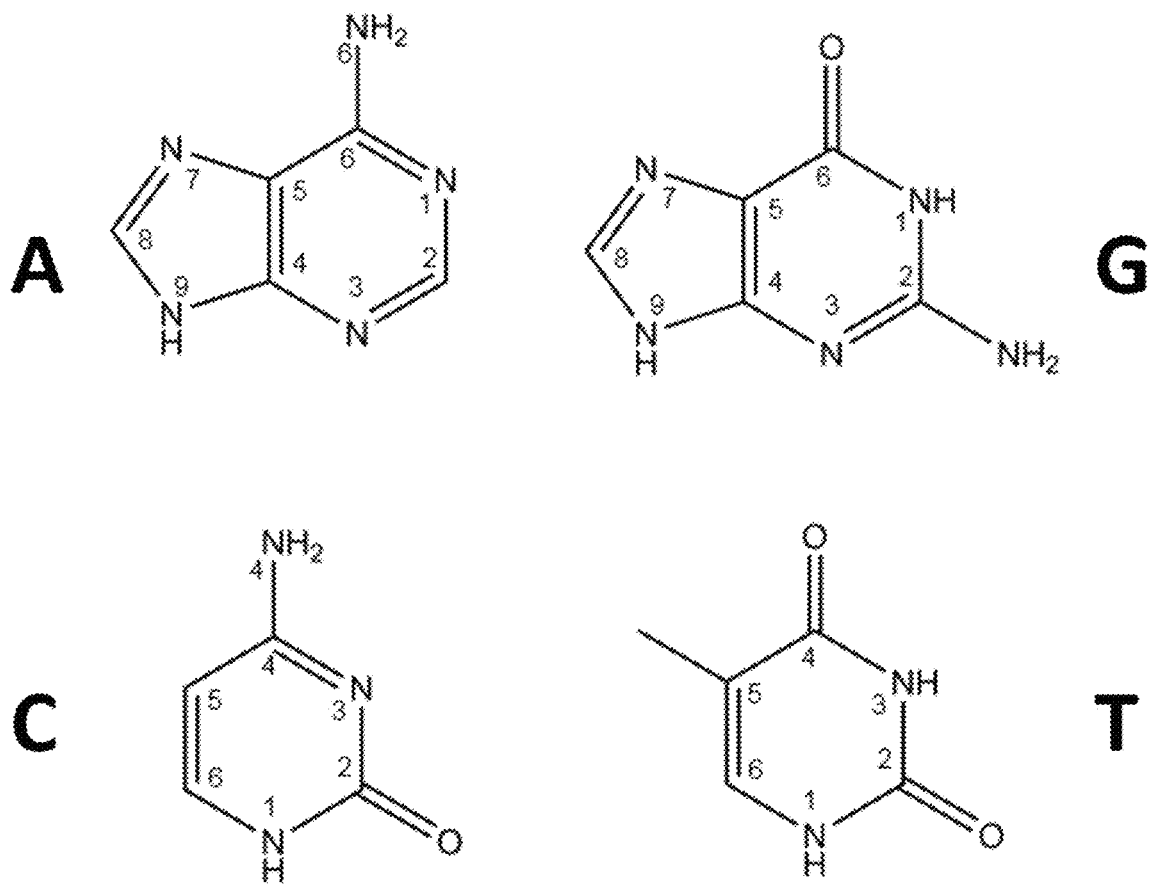
FIG. 5 depicts the biochemical structure of DNA nucleobases A, T, G, and C (including the numbering scheme for molecular bonds).
Figure 6:
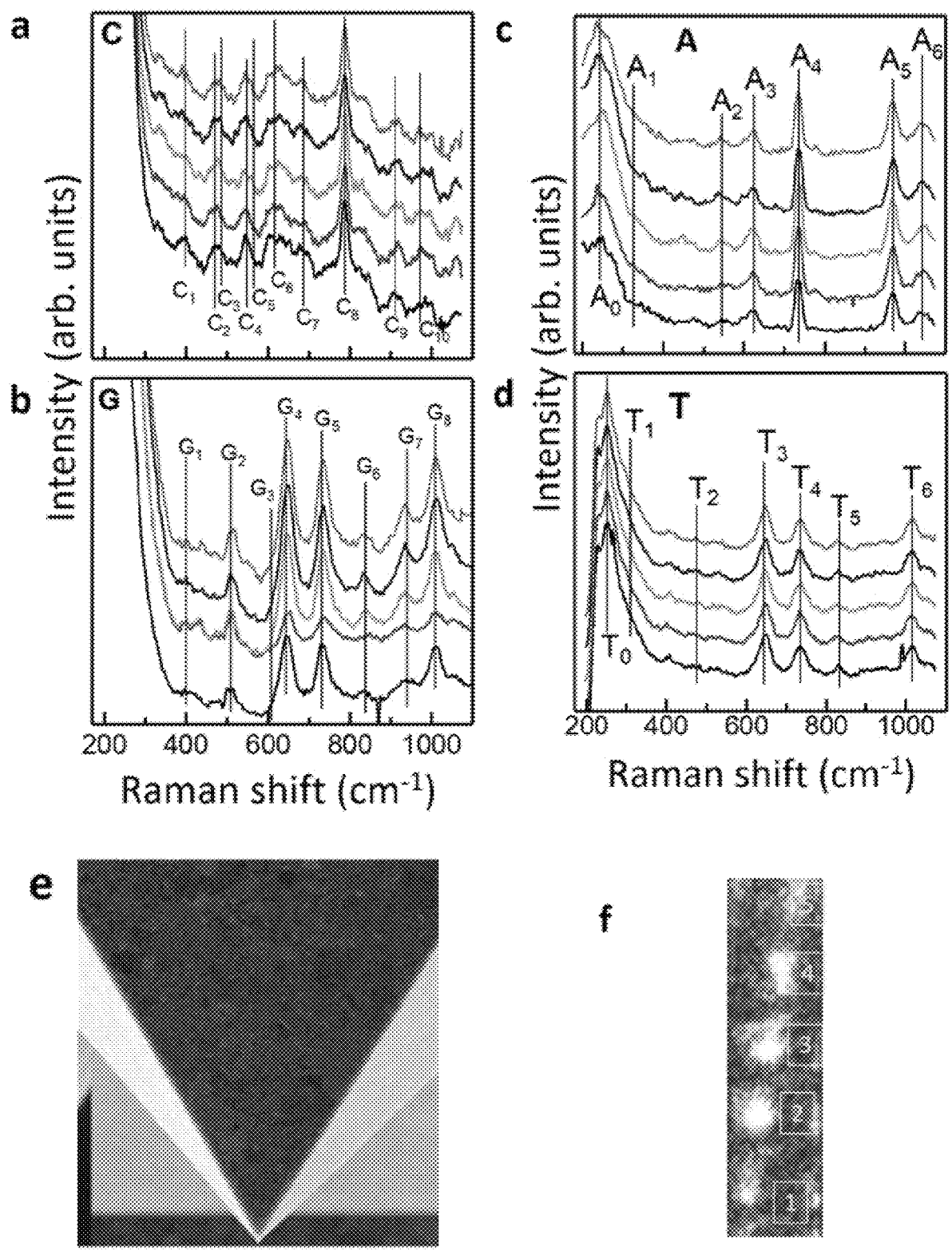
FIG. 6 shows results demonstrating reproducibility of optical fingerprints for DNA k-mers. Raman spectra of homologous DNA oligomers of (Panel a) cytosine, (Panel b) guanine, (Panel c) adenine, and (Panel d) thymine showing the reproducibility of the spectra for five randomly selected nanopyramid tips. (Panel e) Scanning electron micrograph of a nanopyramid tip. (Panel f) Top view of nanopyramid tips as seen in the Raman imaging spectrometer, the individual tips are marked.

Raman spectra for optical fingerprints were collected from four homologous nucleic acid oligomers: $poly(dA)_{16}$, $poly(dG)_{16}$, $poly(dC)_{16}$, and $poly(dT)_{16}$. In these experiments, the spectra contained several vibrational features that are marked as either strong modes ($A_1$, $A_2$, etc.) or weaker modes ($a_1$, $a_2$, etc.). As shown in FIG. 2, Panel a, the strong Raman mode marked $A_1$ occurs due to hydrogen bonding; mode $A_2$ occurs due to a bending mode for C—C=C; mode $A_3$ occurs due to a bending mode for N—C—C; mode $A_4$ occurs due to stretching of C—C and C—N in-phase. The Raman spectra also show mode $A_5$, which occurs due to bending of N—C=N (peak is shifted by ≈20 to 964 $cm^{-1}$). The peak shift can be attributed to the presence of residual water (even after samples are dried) and was expected. The peak corresponding to mode $A_6$ was assigned to the bending mode of C—N—C bonds, but it is shifted by ≈10 $cm^{-1}$ from regular dried adenine nucleotide spectra. A similar shift of ≈10 $cm^{-1}$ occurred for mode $A_7$ due to the bending motion of C2-N1=C6 and the stretching motion of C5-N7=C8 (see details and numbering of the biochemical structure in FIG. 5, Supporting Information), which has been attributed to the presence of water molecules. Some small shifts have also been observed in modes $A_8$ and $A_9$ (stretching modes of C—N and C=N) and were also attributed to the presence of residual water. Other weaker modes with smaller Raman intensities were observed such as $a_1$ (skeletal mode, in-plane), $a_2$ (CH bending, in-plane), and $a_3$. All of these vibrational modes can be used to identify the biochemical structure of the adenine nucleotide, and they are seen reproducibly in multiple tips across the substrate (FIG. 6, Supporting Information). From the thymine spectra shown in FIG. 2, Panel b, clear differences in purine and pyrimidine biochemical species can be seen. Raman modes $T_1$, $T_2$, and $T_3$ occur due to bending vibrations in OH . . . O, N—C=C, and N—C—C bonds. Stretching modes in thymine include $T_4$ due to stretching of C5-CH3, and $T_5$ due to stretching of C4-C5. Two other bending modes observed in the thymine spectra are $T_6$ (due to bending of C—N—C) and $T_7$ (due to bending of N—C—H). Other weaker modes such as $t_1$ and $t_2$ observed for thymine corresponds to bending of C—C=C (in the presence of water) and bending of C5-C—H, respectively. Careful analysis of Raman fingerprints for cytosine (FIG. 2, Panel c) reveals several strong bending modes $C_1$-$C_5$ ($C_1$ due to N3-C2=O and N1-C2=O bending; $C_2$ due to C2-N1-C6 and N3=C4-C5 bending; $C_4$ due to C=C=C and N3=C4-N4 bending; and $C_5$ due to C2-N3=C4 and N1-C2-N3 bending) as well as several strong stretching modes ($C_6$ due to C=O in phase stretch; strongest mode $C_8$ is a breathing mode; $C_{10}$ due to bond C4-C5 stretching). Furthermore, the spectra reveal some weaker bond bending Raman modes c1-c4 (c2 as a result of C5-C4-N4 bending; c3 as a result of C4-C5-H in plane bending; c4 as a result of N1-C6-H in-plane bending). Analyzing the complementary pyrimidine, guanine (FIG. 2, Panel d), we identified bending modes (G1 due to C=O bending; $G_2$ due to N9-C4=C5 and N7-C=C4 bending; gi due to N3-C4=C5 bending; $G_3$ due to C=C=C bending; $G_5$; $g_3$ due to N9-H out-of-plane bending; $G_7$ due to N—C=N and N—C—N bending; $G_8$; $G_9$; $G_{10}$), a breathing mode ($G_4$), and stretching modes ($G_6$ due to C—C stretching; $G_{11}$ due to C2-NH2 stretching). Table 1 summarizes all Raman spectroscopy peaks.

TABLE 1

Raman spectroscopy peaks

| Peak | Shift (cm$^{-1}$) | Assignment |
| --- | --- | --- |
| $A_1$ | 340 | Hydrogen bonding |
| $A_2$ | 537 | C—C=C bend |
| $A_3$ | 622 | N—C—C bend |
| $A_4$ | 737 | C—C and C—N in-phase stretch |
| $A_5$ | 971 | N—C=N bend |
| $A_6$ | 1045 | C—N—C bend |
| $A_7$ | 1140 | C2—N1=C6 bend |
|  |  | C5—N7=C8 stretch |
| $A_8$ | 1320 | C—N stretch |
| $A_9$ | 1350 | C=N stretch |
| $a_1$ | 841 | skeletal mode, in-plane |
| $a_2$ | 1167 | CH bend, in-plane |
| $T_1$ | 304 | OH ... O bend |
| $T_2$ | 467 | N—C=C bend |
| $T_3$ | 647 | N—C—C bend |
| $T_4$ | 737 | C5—CH$_3$ stretch |
| $T_5$ | 832 | C4—C5 stretch |
| $T_6$ | 1017 | C—N—C bend |
| $T_7$ | 1059 | N—C—H bend |
| $t_1$ | 589 | C—C=C bend |
| $t_2$ | 953 | C5—C—H bend |
| $C_1$ | 395 | N3—C2=O and N1—C2=O bend |
| $C_2$ | 468 | C2—N1—C6 and N3=C4—C5 bend |
| $C_4$ | 538 | C=C=C and N3=C4—N4 bend |
| $C_5$ | 558 | C2—N3=C4 and N1—C2—N3 bend |
| $C_6$ | 611 | C=O in-phase stretch |
| $C_8$ | 788 | Breathing mode |
| $C_{10}$ | 973 | C4—C5 stretch |
| $c_2$ | 715 | C5—C4—N4 bend |
| $c_3$ | 1000 | C4—C5—H in-plane bend |
| $c_4$ | 1028 | N1—C6—H in-plane bend |
| $G_1$ | 402 | C=O bend |
| $G_2$ | 511 | N9—C4=C5 and N7—C=C4 bend |
| $G_3$ | 604 | C=C=C bend |
| $G_4$ | 648 | Breathing mode |
| $G_6$ | 847 | C—C stretch |
| $G_7$ | 931 | N—C=N and N—C—N bend |
| $G_{11}$ | 1226 | C$_2$—NH$_2$ stretch |
| $g_1$ | 548 | N3—C4=C5 bend |
| $g_3$ | 866 | N9—H out-of-plane bend |

Reproducibility of optical fingerprints from Raman spectroscopy was established by characterizing peaks obtained from several tips in the million-plexed device (over $4 \times 10^6$ tips were fabricated on each substrate using optical lithography), by changing the field of view and looking at several tips individually. In FIG. 6, we present Raman spectroscopy data for all four DNA nucleotides from randomly selected nanopyramids. For a given spectrum, the autocorrelation ratios of the various peaks are fairly constant and exhibit very small variations in signal (relative peak heights) from tip to tip (FIG. 4). It is helpful to establish the amount of signal amplitude variation between the tips and further establish that the ratios of the Raman vibrational features remain constant from peak to peak. It is also helpful to point out that for high-throughput sequencing applications, neither collecting spectra with extremely low signal-to-noise nor scanning the entire fingerprinting window is necessary. High accuracy can be achieved with simple measurements, as we demonstrate later.

We also collected FTIR spectra for each nucleobase from the four homologous nucleic acid oligomers (FIG. 2) and identified several important peaks. While some peaks were common between Raman and FTIR spectra (e.g., comparing adenine optical fingerprints in FIG. 2 Panel a, $\alpha_2$ and $A_4$ modes both show bending motion of C—C and C—N bonds in-phase, $\alpha_5$ and $A_5$ modes show the bending motion of the N—C=N bond, and $\alpha_7$ and $A_7$ modes show bending motion of C2-N1=C6 and the stretching motion of C5-N7=C8), several new complementary modes (e.g., adenine FTIR fingerprints $\alpha_1$, $\alpha_3$, $\alpha_4$, $\alpha_6$, $\alpha_8$, $\alpha_9$, $\alpha_{10}$, $\alpha_{11}$, $\alpha_{12}$, and $\alpha_{13}$) are seen in the FTIR spectra. For example, modes $\alpha_{10}$ and $\alpha_{13}$, which are not seen in Raman spectra; $\alpha_{10}$ occurs due to the stretching mode of the imidazole ring, and $\alpha_{13}$ shows the bending mode of NH$_2$. Similarly, the modes $\alpha_3$ (C—C stretching), $\alpha_4$ (N9-H out-of-plane bending), $\alpha_9$ (C2-H and C8-H out-of-plane bending, and N=C—H bending), $\alpha_1$ (C—N9-H bending), $\alpha_{12}$ (C=N and C=C stretching) are weak and unlikely to be observed in Raman spectra, but are strongly seen in corresponding FTIR spectra. Therefore, when combined together, Raman and FTIR spectra can provide unique and complementary biochemical optical fingerprints for DNA sequencing.

Cytosine, guanine, and thymine also show peaks in the FTIR spectra (FIG. 2, Panels b-d) that are not seen in Raman spectra due to small peak intensities. In cytosine, peak $X_1$ arises due to N—H out-of-plane bending and is not seen in Raman optical spectra. Peaks $X_3$ (NH2 rocking), $X_4$ (C4-N4 stretching), $X_5$ (C=C—H bending), $X_6$ (C4-N3 and C2-N3 stretching), $X_7$ (C4=N3 and C4-N4 stretching), $X_8$ (C5=C6 stretching), and $X_9$ (NH2 bending) are not observed prominently in Raman spectra likely due to small intensities. In thymine, peak $T_2$ occurs due to out-of-plane N—H bending, whereas peak $T_{12}$ occurs due to stretching of C4=O and C2=O. Both of these peaks are Raman inactive. Furthermore, peaks $T_7$ (C—N stretching), $T_9$, and $T_{10}$ (broad N1-H and N3-H bending) have much stronger peaks in FTIR than in Ramen spectra. Similar analysis of guanine shows peaks $\gamma_1$ and $\gamma_3$ (N1-H bending) are Raman inactive, whereas peaks $\gamma_2$ (ring bending), $\gamma_4$ (C—C stretching), $\gamma_6$ (NH2 rocking), $\gamma_{10}$ (N7=C8 and C8-C9 stretching), $\gamma_{12}$ (C=O stretching), and $\gamma_{13}$ (C=O stretching and NH2 bending) have stronger intensities in the FTIR spectrum. Table 2 summarizes all FTIR spectroscopy peaks.

TABLE 2

FTIR spectroscopy peaks

| Peak | Wavenumber (cm$^{-1}$) | Assignment |
| --- | --- | --- |
| $\alpha_2$ | 727 | C—C and C—N in-phase bend |
| $\alpha_3$ | 807 | C—C stretch |
| $\alpha_4$ | 869 | N9—H out-of-plane bend |
| $\alpha_5$ | 952 | N—C=N bend |
| $\alpha_7$ | 1129 | C2—N1=C6 bend |
|  |  | C5—N7=C8 stretch |
| $\alpha_9$ | 1371 | C2—H and C8—H out-of-plane bend |
|  |  | N=C—H bend |

TABLE 2-continued

FTIR spectroscopy peaks

| Peak | Wavenumber (cm$^{-1}$) | Assignment |
|---|---|---|
| $\alpha_{10}$ | 1460 | Imidazole ring stretch |
| $\alpha_{11}$ | 1507 | C—N9—H bend |
| $\alpha_{12}$ | 1620 | C=N and C=C stretch |
| $\alpha_{13}$ | 1650 | NH$_2$ bend |
| $\tau_2$ | 861 | N—H out-of-plane bend |
| $\tau_7$ | 1227 | C—N stretch |
| $\tau_9$ | 1511 | N1—H and N3—H bend |
| $\tau_{12}$ | 1750 | C4=O and C2=O stretch |
| $\chi_1$ | 813 | N—H out-of-plane bend |
| $\chi_3$ | 1077 | NH$_2$ rocking |
| $\chi_4$ | 1235 | C4—N4 stretch |
| $\chi_5$ | 1361 | C=C—H bend |
| $\chi_6$ | 1458 | C4—N3 and C2—N3 stretch |
| $\chi_7$ | 1519 | C4=N3 and C4—N4 stretch |
| $\chi_8$ | 1626 | C5=C6 stretch |
| $\chi_9$ | 1708 | NH$_2$ bend |
| $\gamma_2$ | 712 | Ring bend |
| $\gamma_3$ | 804 | Ni—H bend |
| $\gamma_4$ | 860 | C—C stretch |
| $\gamma_6$ | 1056 | NH$_2$ rocking |
| $\gamma_{10}$ | 1493 | N7=C8 and C8—C9 stretch |
| $\gamma_{12}$ | 1660 | C=O stretch |
| $\gamma_{13}$ | 1698 | C=O stretch |
|  |  | NH$_2$ bend |

To be useful as a sequencing platform, our proposed BOS method must be able to decipher mixed DNA sequences (those containing a mix of all bases A, G, C, and T, as opposed to merely the homologous sequences used for developing fingerprints as described above). Differences in respective Raman cross-sections between the various DNA nucleotides, as well as conformational entropy, pose important challenges for facile sequencing of mixed DNA sequences using optical fingerprints. In the Raman spectra for a repeating 4-mer DNA oligomer poly(dATGC)$_4$ in FIG. 2, Panel e, peaks can be seen from adenine ($A_0$, $A_1$, $A_2$, $A_3$, $A_4$, $A_5$, and $A_6$), guanine ($G_1$, $G_3$, $G_4$, $G_5$, $G_6$, $G_8$ and $G_9$), cytosine ($C_1$, $C_2$, $C_4$, $C_5$, $C_7$, $C_8$, and $C_9$), and thymine ($T_0$, $T_3$, $T_4$, $T_5$, and $T_6$). While the linearity of peaks with varying amounts of respective nucleotide content has been shown in ensemble studies, where the different conformation and orientation effects cancel out, it can pose a challenge for single-molecule spectra for BOS. Also, since the resulting plasmonic interaction can vary strongly depending on strength of plasmon enhancement (between nanoparticles and different plasmonic structures), the reproducibility in design of tips may be useful for the development of reproducible and robust sequencing. We have already shown that between different substrates made from the same mold, there is reproducible plasmon enhancement and vibrational spectroscopic features (FIGS. 4 and 6), which was also seen in prior studies using template stripped structures. Therefore, we use this reproducibility to identify the nucleobase content in mixed DNA k-mers, which includes nucleobases present and their relative fraction.

Figure 3:
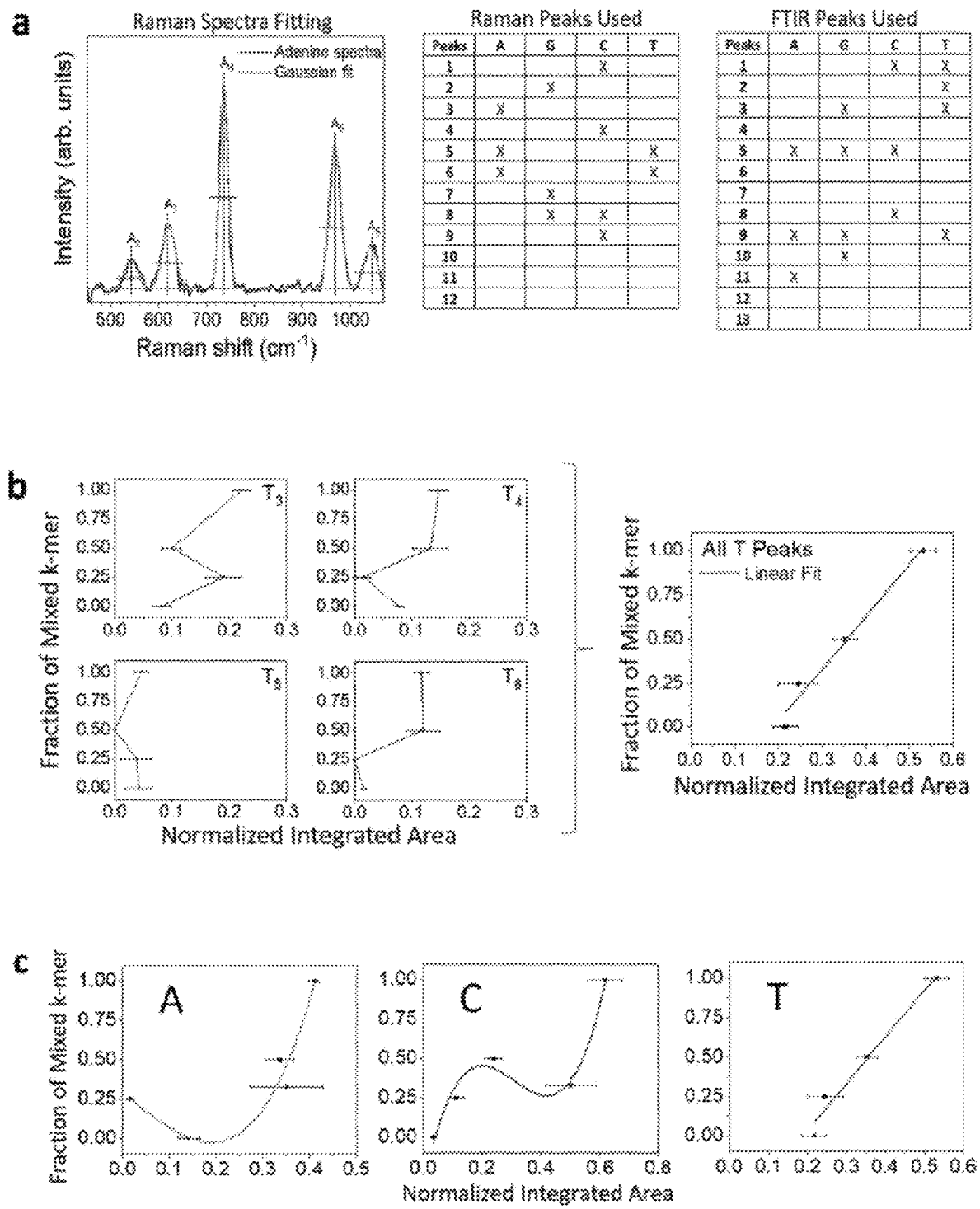
FIG. 3, Panels a-g shows base calling DNA k-mer blocks.
Figure 3:
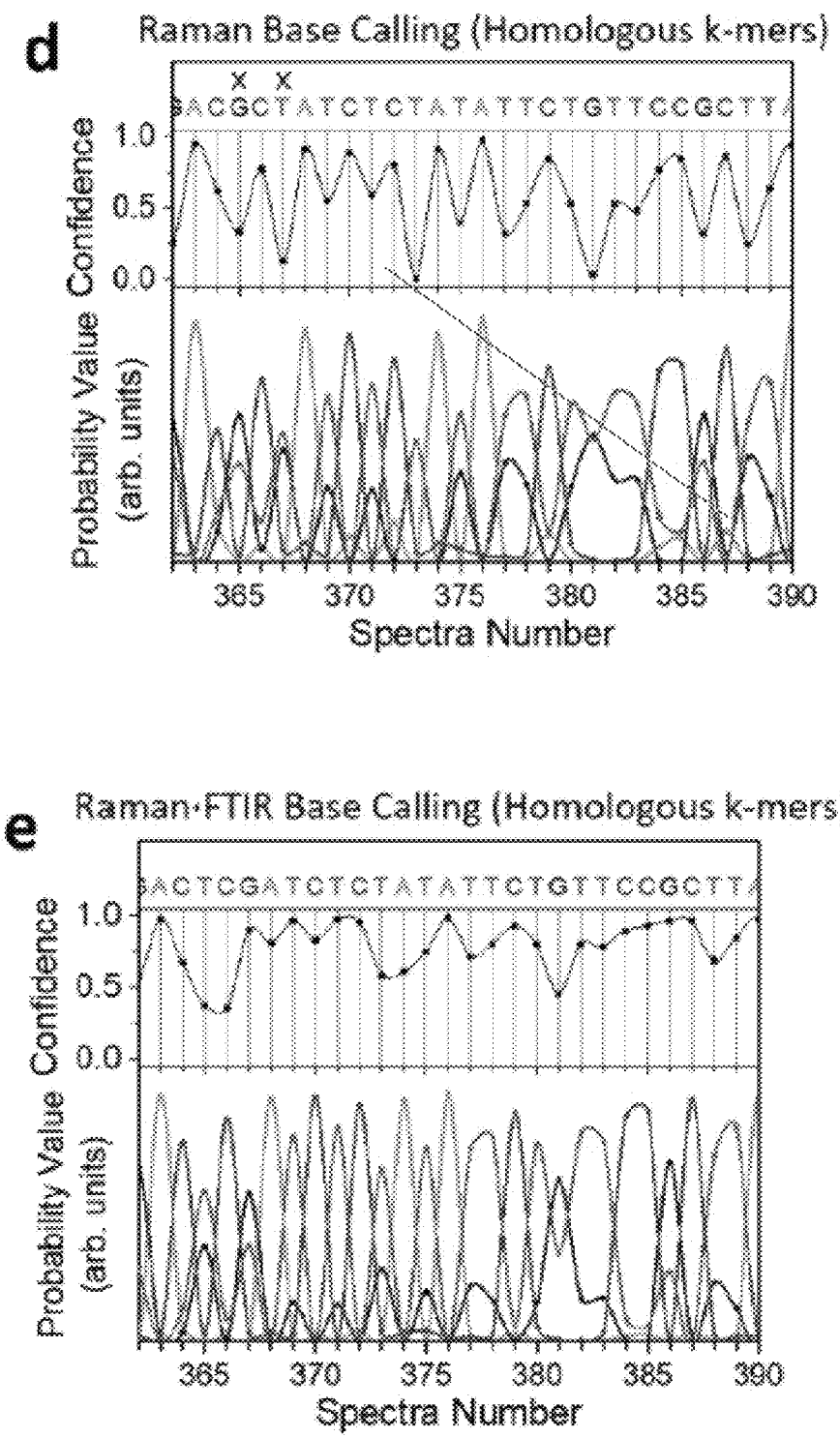
Figure 3:
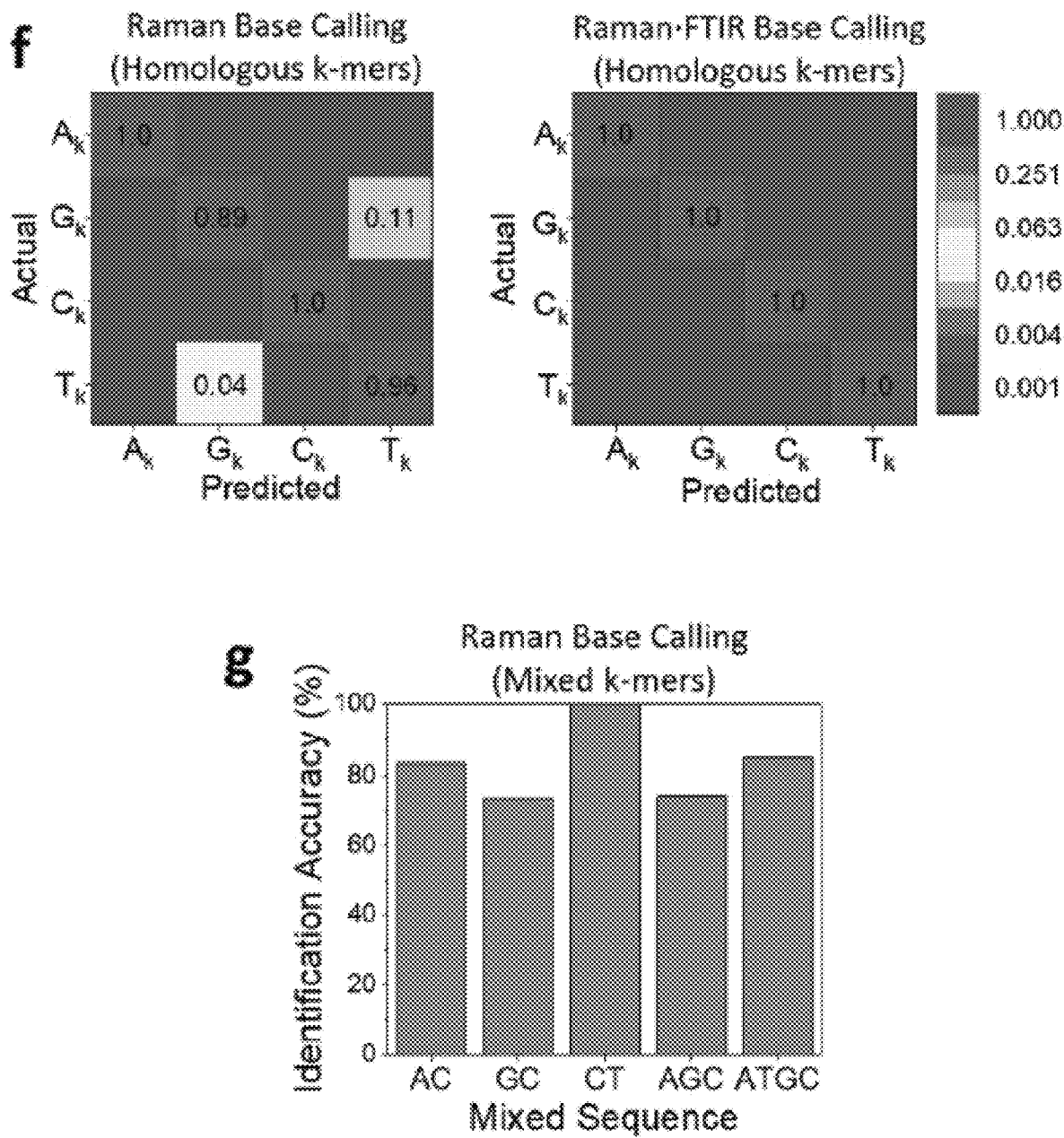

To analyze our ability to identify nucleobases from their characteristic spectra (base calling), we developed algorithms described below in the Experimental Section and FIG. 3, Panels a-c. To establish fingerprints, Gaussian curves were fit to block k-mer spectra (Raman and FTIR) from homologous sequences, allowing the center location and corresponding full width at half maximum to be determined for each characteristic peak in the spectra (i.e., adenine in FIG. 3, Panel a). For homologous k-mer block identification, only a subset of spectra peaks for each nucleobase are considered (also noted in FIG. 3, Panel a), and base calls are then made for whichever nucleobases show the largest intensity (largest integrated area) in the unknown spectra. To identify the nucleobases present in mixed k-mer blocks, we used specific Raman peaks that consistently appear when each of the nucleobases is in a given k-mer ($A_3$, $A_4$, $A_5$; $G_4$, $G_6$; $C_8$; $T_3$, $T_4$). Following identification of which nucleobases are present, relative fractions can be determined from known correlations of calculated Raman peak intensity (integrated area under the curve for all major peaks) with actual mix fraction (FIG. 3, Panels b and c). Note that only three correlations (A, C, T) are needed as the fourth (G) is determined from the remainder.

Figure 7:
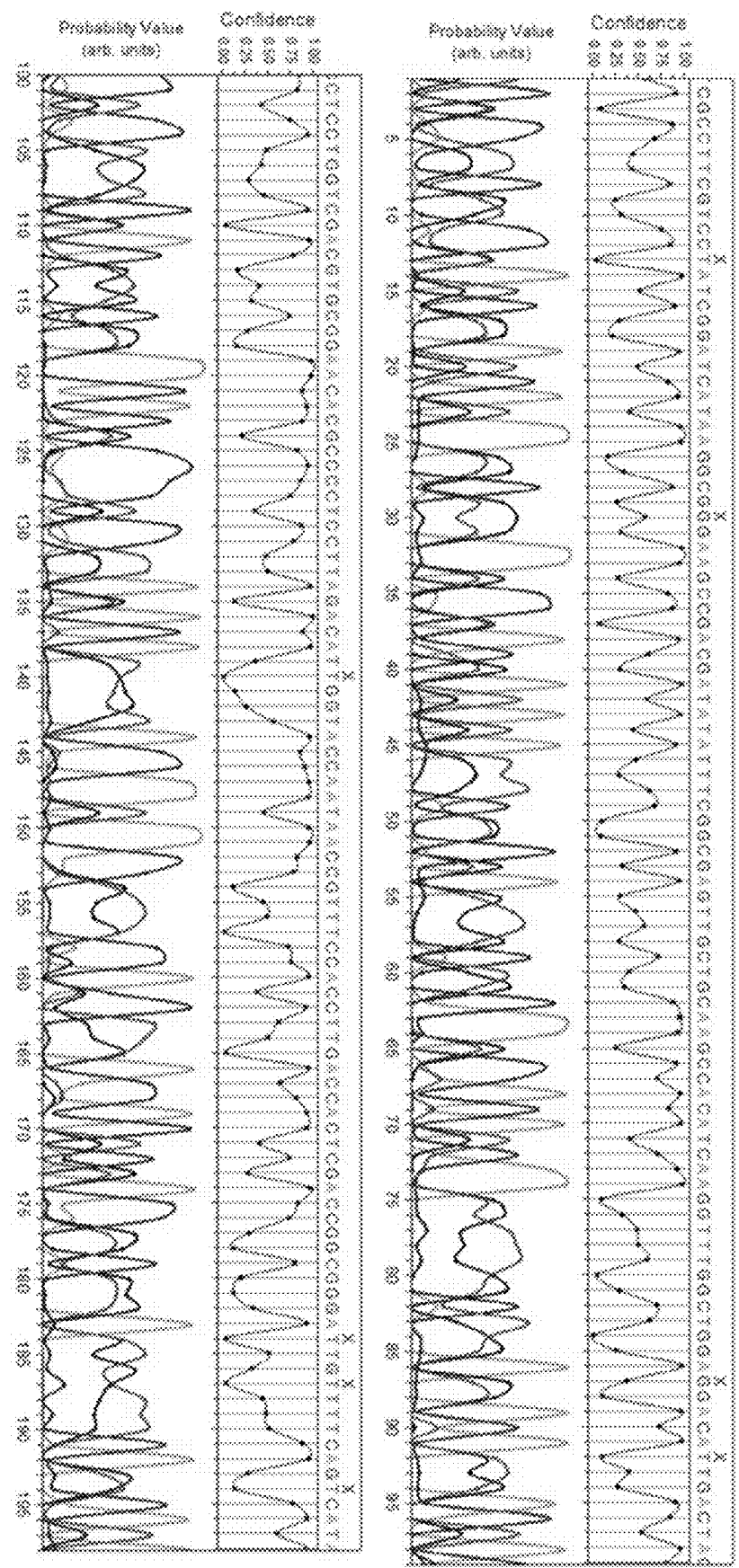
FIG. 7 shows the probability values and confidence for base calling homologous k-mer blocks with Raman spectroscopy (SEQ ID NOs:12-15). Numbers correlate with those in FIG. 8.
Figure 7:
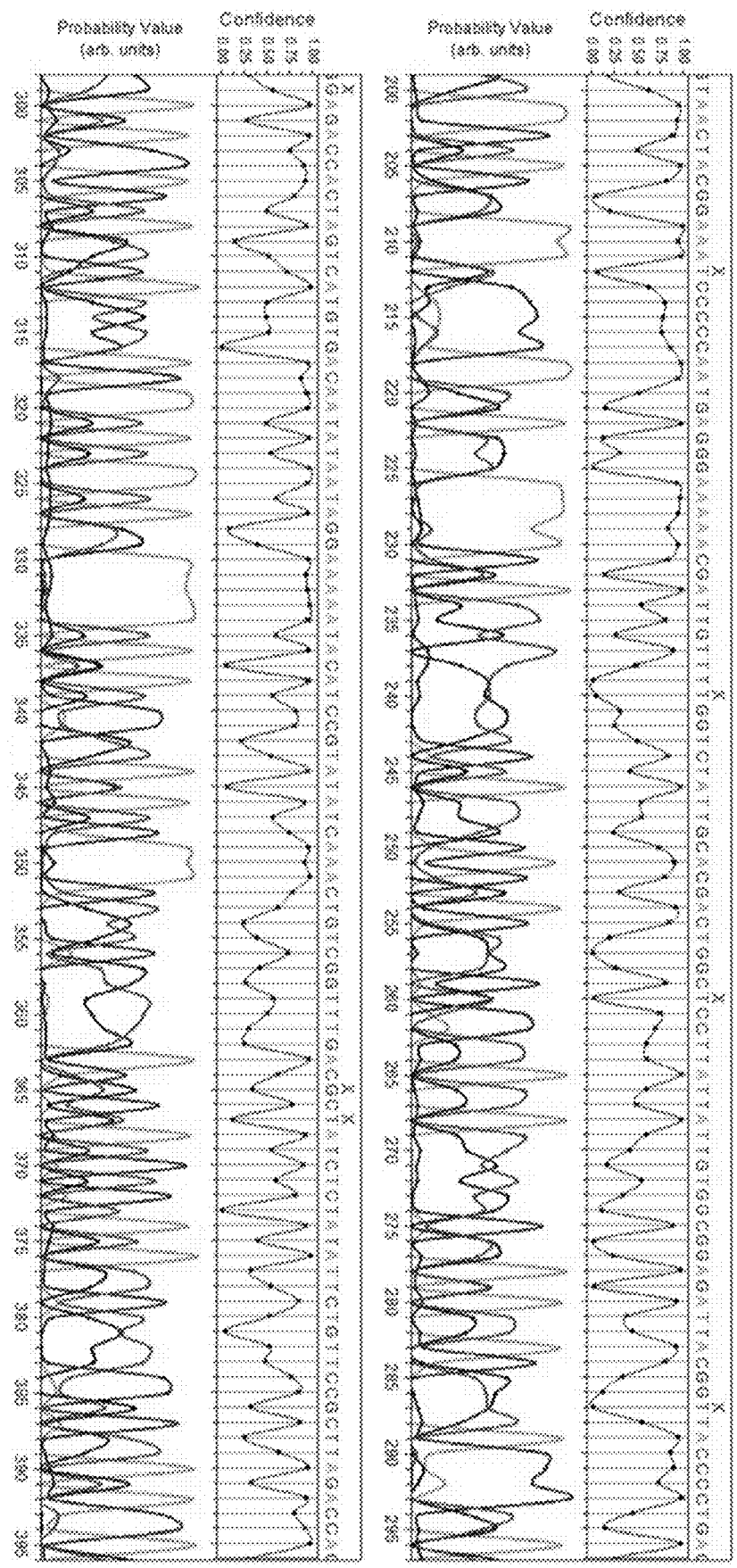
Figure 8:
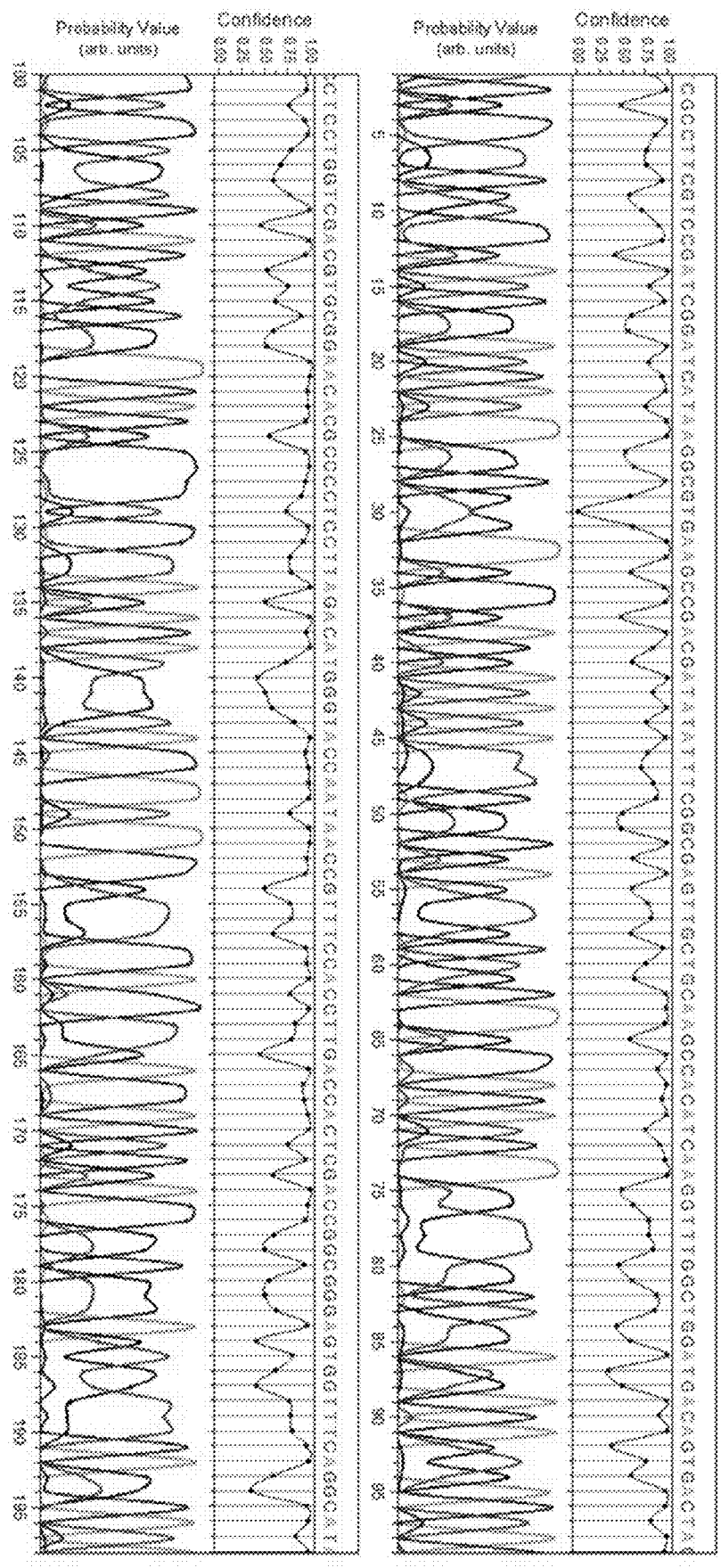
FIG. 8 shows probability values and confidence for base calling homologous k-mer blocks with combined Raman and FTIR (SEQ ID NOs:16-19). Numbers correlate with those in FIG. 7.
Figure 8:
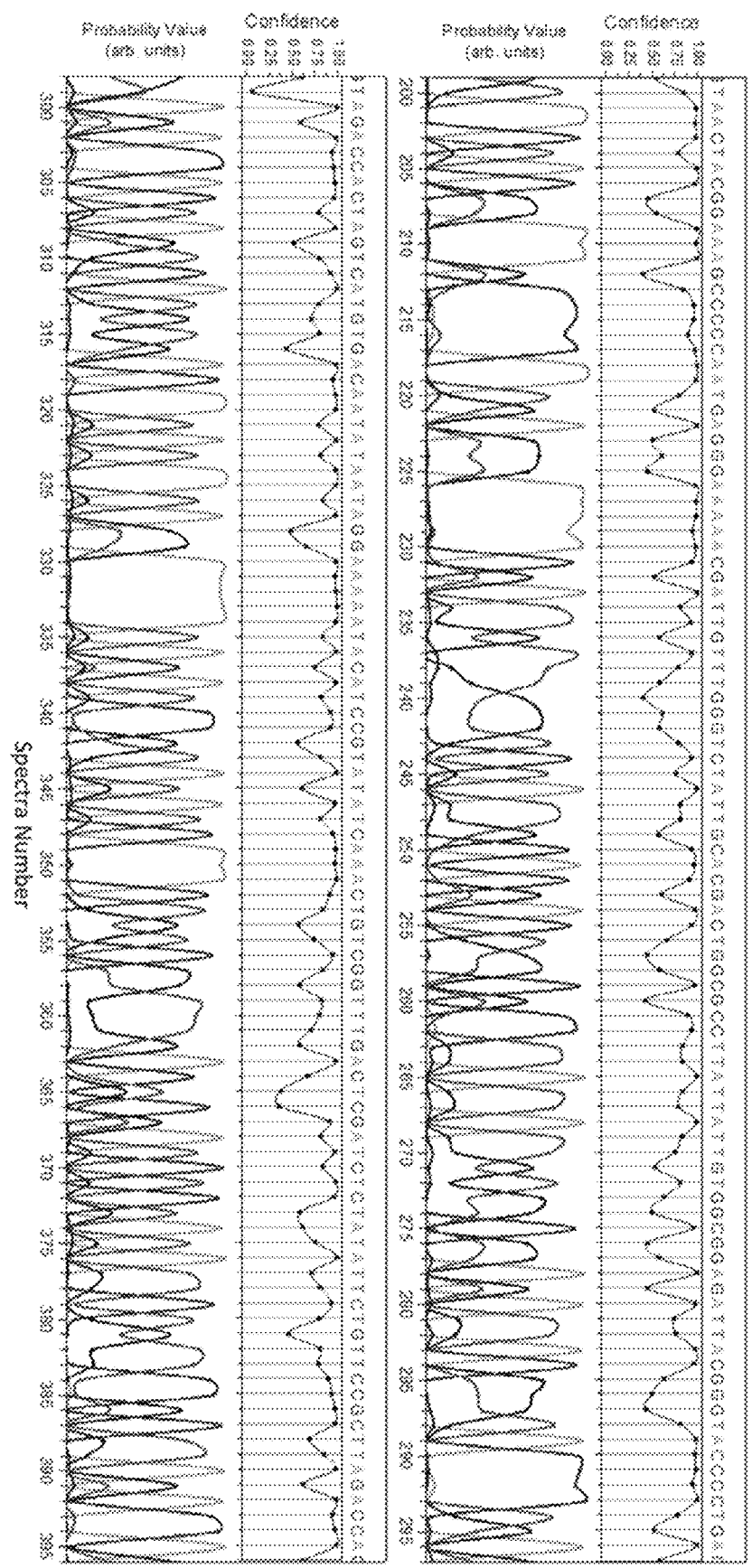

To test the algorithms and support our proposed optical DNA sequencing method, we input known sequence block k-mer spectra into the algorithms as though they were unknown and observed if correct base calls were made. For homologous sequences, 99 measured spectra for each A, T, G, and C (396 total spectra from single pixels) were used for testing the BOS algorithmic method. When only relying on Raman spectroscopy, we correctly base-called 100% of A and C k-mer spectra, 88.9% of G k-mer spectra, and 96.0% of T k-mer spectra. When Raman spectroscopy and FTIR spectroscopy were combined, we achieved 100% base calling accuracy for all A, T, G, and C k-mers. Base calling for a subset of 28 spectra is shown in FIG. 3, Panels d and e, and for all 396 total spectra in FIGS. 7 and 8. The advantage of using the two complementary vibrational spectroscopy techniques can also be seen when analyzing the base calling performance using confusion matrices (FIG. 3, Panel f). This method characterizes not only the accuracy of correct base calls but also false-positive and false-negative calls. When comparing the confusion matrix analysis of Raman and combined Raman-FTIR spectroscopy, we observed clear improvement in base calling accuracies using the combined spectra, especially for guanine and thymine nucleobases. To further quantify the precision of DNA base calling from optical spectroscopy measurements, we used confidence in base calling as another important metric in addition to call accuracy. The confidence in calling a particular base can be calculated using the probability values from the base calling algorithm: $C_i = (P_i - P_j)/P_i$. Here, $C_i$ is the confidence for calling base i, $P_i$, is the probability value associated with the called base, and $P_j$ is the second highest probability (for the second most probable base). This confidence also characterizes the signal-to-noise level. As highlighted in FIG. 3, Panels d and e, combining Raman and FTIR data not only improves accuracy, but increases confidence for base calling all nucleobases (A: 0.948 (±0.02) to 0.980 (±0.01), G: 0.196 (±0.12) to 0.539 (±0.08), C: 0.798 (±0.12) to 0.937 (±0.04), T: 0.478 (±0.14) to 0.758 (±0.13)). For mixed sequences, a variety of DNA oligomers were analyzed: poly(dAC)$_8$, poly(dGC)$_8$, poly(dCT)$_8$, poly(dAGC)$_5$, and poly(dATGC)$_4$. FIG. 3, Panel g shows our ability to identify which nucleobases are present in a mixed k-mer at an average of 79% accuracy from single pixels. This mixed sequence recognition analysis provides additional evidence for block optical DNA sequencing. Applicability could be further expanded to include epigenetic analyses, since previous studies have shown the ability of Raman spectroscopy to detect modified nucleobases.

As previously noted, the nanometer-scale mode volumes demonstrated for SERS and TERS permit the collection of spectra from single DNA molecules; however, the angstrom scale nucleotides prevent single letter resolution for DNA sequencing. We have therefore demonstrated that a robust optical vibrational spectroscopic method (namely, Raman spectroscopy, and also coupled Raman and FTIR spectroscopy) can be used to acquire fingerprints of DNA nucleobases, and be applied to achieve accurate identification of mixed sequence DNA k-mers. This paves the way for a BOS method (FIG. 1, Panel a), where k-mer blocks are read instead of single letters. Although single letters are not directly determined, a sequence can be deduced from a raster scanning approach. Furthermore, BOS can be applied for high-throughput identification of specific genes and biomarkers, for example in embodiments and applications where an exact sequence identity is not necessary. For example, a 5-8 nm resolution for a single-stranded DNA sample (≈4-6 Å inter nucleotide separation) will lead to the identification of 8- to 12-mers, or blocks of 8-12 DNA nucleotides. For a DNA sequence of length N, the expected number of random matches to a particular k-mer is given by the expression $(N-k+1)/4^k$. To find a unique k-mer (i.e., a k-mer that is expected to occur only a single time or less) in a sequence of length N, the expression can be made into an inequality $$\frac{N-k+1}{4^k} \leq 1$$

and solved for k. For a human genome ($N=3\times10^9$ base pairs), $k \approx 16$ meaning that a particular 16-mer is expected to occur only once within the genome.

Since BOS gives A, T, G, and C content, rather than a specific sequence, for signal detection from 10-mers the least number of continuous BOS reads giving a unique block in a genome would be two if the 10-mers were all the same letter (e.g., AAAAAAAAAA, SEQ ID NO. 1, or ten T's, G's, or C's in any order). When the 10-mers are of a single nucleobase, there are no other possible permutations and the expectation of seeing the 10-mer is $$\frac{1}{4}\times\frac{1}{4}\times\frac{1}{4}\times\frac{1}{4}\times\frac{1}{4}\times\frac{1}{4}\times\frac{1}{4}\times\frac{1}{4}\times\frac{1}{4}\times\frac{1}{4} = 1/4^{10}.$$

Therefore, two continuous 10-mers need $$\frac{3\times10^5 - 10 + 1}{(4^{10})^2} = \frac{3\times10^9}{1.1\times10^{12}} < 1$$

to be detected. For cases with one different nucleobase within the 10-mer, there is a probability of other permutations giving rise to the same BOS signal. For example, nine A's and one C in any order leads to an expectation of $$\frac{\left(\frac{10!}{9!1!}\right)}{4^{10}} = \frac{10}{4^{10}}$$

since the C can be placed in ten possible places, each leading to different sequences with the same BOS signal. For other combinations of 10-mers, expectation is even higher. For instance, seven A's, one C, one T, and one G (in any order) yields the same spectra and leads to an expectation of $$\frac{\left(\frac{10!}{7!1!1!1!}\right)}{4^{10}} = \frac{720}{4^{10}}$$

due to the 720 possible 10-mer permutations. The highest number of possible permutations for a 10-mer (leading to the most continuous BOS reads necessary to achieve a unique sequence) occurs with three nucleotides each for two of the letters (e.g., A and T) and two nucleotides each for the other two letters (e.g., G and C), where the expectation is $$\frac{\left(\frac{10!}{3!3!2!2!}\right)}{4^{10}} = \frac{25200}{4^{10}}.$$

Even in this worst case, only three or four continuous 10-mers will need to be read for a unique sequence identification within a genome, and hence positive identification of a specific gene. Therefore, merely finding A, T, G, and C content information for individual DNA k-mers leads to loss of exact single-letter positions (lossy data compression), but the DNA sequence can still be uniquely identified and converted to useful information.

TABLE 3

10-mer sequential blocks for a partial sequence of TEM-1 β-lactamase gene in *E. Coli*.

| k-mer number | Sequence | A/T/G/C content | Cumulative number of random matches | |
|---|---|---|---|---|
| 1 | ATGAGTATTC | 3/4/2/1 | $5.5 \times 10^4$ | SEQ ID NO: 2 |
| 2 | AACATTTCCG | 3/3/1/3 | $8.9 \times 10^2$ | SEQ ID NO: 3 |
| 3 | TGTCGCCCTT | 0/4/2/4 | $2.7 \times 10^0$ | SEQ ID NO: 4 |
| 4 | ATTCCCTTTT | 1/6/0/3 | $2.1 \times 10^{-3}$ | SEQ ID NO: 5 |
| 5 | TTGCGGCATT | 1/4/3/2 | $2.6 \times 10^{-5}$ | SEQ ID NO: 6 |
| 6 | TTGCCTTCCT | 0/5/1/4 | $3.1 \times 10^{-8}$ | SEQ ID NO: 7 |
| 7 | GTTTTTGCTC | 0/6/2/2 | $3.7 \times 10^{-11}$ | SEQ ID NO: 8 |
| 8 | ACCCAGAAAC | 5/0/1/4 | $4.4 \times 10^{-14}$ | SEQ ID NO: 9 |
| 9 | GCTGGTGAAA | 3/2/4/1 | $5.3 \times 10^{-16}$ | SEQ ID NO: 10 |
| 10 | GTAAAGATG | 5/2/3/0 | $1.3 \times 10^{-18}$ | SEQ ID NO: 11 |

As an example, a partial (first 100 nucleotide) sequence of the TEM-1 β-lactamase gene from *Escherichia coli* (*E. coli*) is broken down into 10-mer blocks in Table 3. The table shows the nucleotide content of each 10-mer and the cumulative expected number of random matches in the *E. coli* genome of $4.6\times10^6$ base pairs. For BOS analysis reading sequential k-mer blocks, a unique sequence is reached at the fourth k-mer, meaning that this gene could be identified in four measurements. We further demonstrate that nonsequential, randomized block k-mer identifications can still lead to high-throughput gene identification. Table 4 shows the same partial sequence of the TEM-1 β-lactamase gene, this time with randomized order of the 10-mer blocks. As calculated in the table, a unique sequence is reached again after merely four measurements (with other randomized orders, the maximum number of necessary reads is five). Therefore, BOS is a different method of sequence and gene identification that offers simultaneous lossy data compression. This high-throughput optical detection and data compression can help increase the throughput and speed of DNA sequencing and be a valuable assay for quickly extracting useful genomic information.

TABLE 4

10-mer randomized blocks for a partial sequence TEM-1 β-lactamase gene in E. Coli.

| k-mer number | Sequence | A/T/G/C content | Cumulative number of random matches |
|---|---|---|---|
| 2 | AACATTTCCG | 3/3/1/3 | $7.4 \times 10^4$ |
| 10 | GTAAAGATG | 5/2/3/0 | $8.0 \times 10^3$ |
| 6 | TTGCCTTCCT | 0/5/1/4 | $2.6 \times 10^1$ |
| 8 | ACCCAGAAAC | 5/0/1/4 | $5.4 \times 10^{-2}$ |
| 9 | GCTGGTGAAA | 3/2/4/1 | $7.7 \times 10^{-4}$ |
| 1 | ATGAGTATTC | 3/4/2/1 | $7.8 \times 10^{-6}$ |
| 5 | TTGCGGCATT | 1/4/3/2 | $5.3 \times 10^{-8}$ |
| 3 | TGTCGCCCTT | 0/4/2/4 | $6.0 \times 10^{-11}$ |
| 4 | ATTCCCTTTT | 1/6/0/3 | $1.1 \times 10^{-14}$ |
| 7 | GTTTTTGCTC | 0/6/2/2 | $1.3 \times 10^{-18}$ |

We present a new and unconventional approach for high throughput, BOS of DNA in a process that is enzyme- and label-free. BOS uses multiplexed nanoscale pyramid patterns as a probe and incorporates simultaneous lossy data compression by measuring the A, T, G, and C content in DNA k-mer blocks, instead of traditional single-letter sequences. We acquired surface-enhanced Raman spectroscopy (with coupled FTIR spectroscopy) vibrational fingerprints for DNA nucleobases. The reproducible optical fingerprints and signal enhancement from each nanopyramid tip demonstrates the robustness of this method in circumventing the problem of signal uncertainties in other single-molecule DNA sequencing approaches. Using fingerprints generated from homologous DNA oligomers, we obtained high accuracy and confidence in identifying the content of mixed DNA k-mer sequences, with our algorithmic approach to base calling. Furthermore, we demonstrated that using information of A, T, G, and C content of sequential DNA blocks can serve as an alternative to single letter sequencing, while randomized block content can be useful for rapid identification of genes and other biomarkers in a high-throughput manner (≈4-5 reads required). This method can be a promising tool in developing more rigorous quantitative technologies that achieve single-nucleotide sensitivity in optical DNA sequence based assays. While most biomarker discovery techniques today rely on amplification and other biochemical treatments, our results pave the way for high-throughput optical tools for single-molecule studies with important biotechnology applications. BOS gene identification methods could be directly applied to rapid genotyping in molecular and evolutionary biology, metagenomics, medical diagnostics, and DNA profiling.

Materials and Methods

Figure 9:
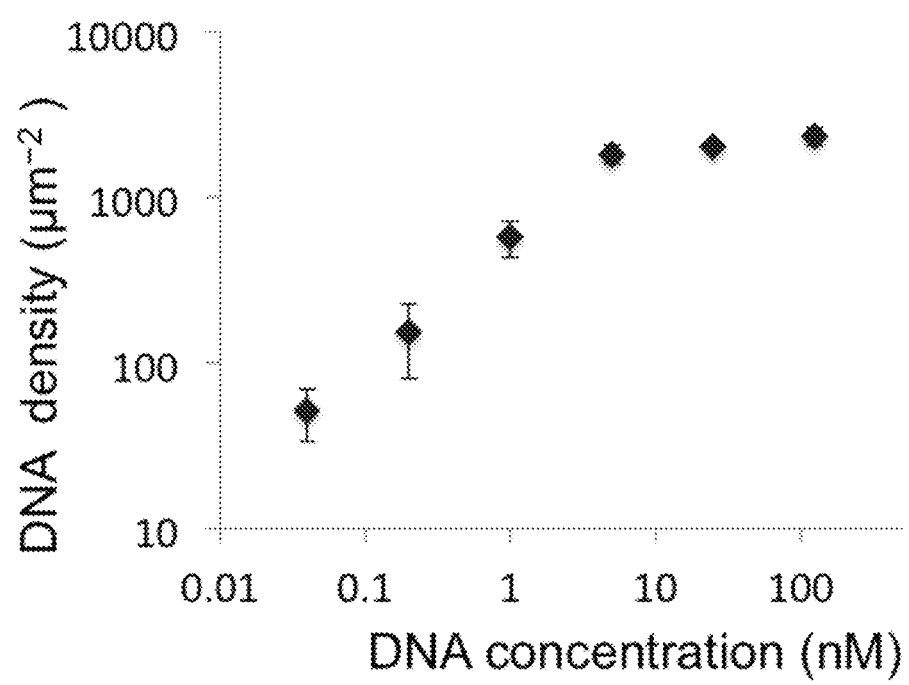
FIG. 9 is a graph of DNA surface density vs. concentration. Concentration series of apparent DNA surface density as a function of DNA concentration for a fixed time of t=5 min onto a cysteamine surface substrate. Each point represents the mean surface density determined by averaging the number of molecules per area in several images corresponding to different areas of the surface (AFM imaging and semi-automated image analysis with Gwyddion). The error bars represent +/− the standard deviation between different areas of the surface in the same experiment.

Preparation of Multiplexed Optical Reader:

Plasmonic nanopyramid arrays were fabricated as multiplexed optical probes using optical lithography, self-limited anisotropic chemical etching with potassium hydroxide, and metal deposition followed by template stripping. Briefly, circular patterns with 2 μm periodicity were designed using optical lithography and were patterned on a silicon (100) substrate using a metal mask. With self-limiting anisotropic KOH etching, inverted sharp nanopyramids were etched in silicon and used as a template. Using thermal metal evaporation, a 200 nm thick layer of silver was evaporated onto cleaned templates, and peeled off using an epoxy backing layer. Sample Preparation: Single-stranded DNA oligomers (e.g., poly(dA)$_{16}$, poly(dC)$_{16}$, poly(dG)$_{16}$, poly(dT)$_{16}$, poly (dATGC)$_4$, poly(dAC)$_8$, poly(dGC)$_8$, poly(dCT)$_8$, and poly (dAGC)$_5$) were purchased from Invitrogen, USA, suspended in ultrapure deionized (DI) water obtained from a Barnstead Thermolyne NANOpure Diamond purification system equipped with a UV lamp-water resistivity >18 MΩ cm ($10 \times 10^{-9}$ to $100 \times 10^{-9}$ M, measured using a nanodrop spectrophotometer), and dropcasted onto the multiplexed readers. For contamination studies, dATP and glycine were mixed at varying molar ratios ($1 \times 10^{-3}$ to $5 \times 10^{-3}$ m) in DI water and drop-casted onto a flat glass substrate. Samples were left to dry in air prior to analysis. See FIG. 9 for DNA surface density discussion.

Multiplexed Imaging and Optical Vibrational Spectroscopy (Raman and FTIR):

The Raman spectra of DNA, benzenethiol, and nucleotideglycine mixtures were acquired using a home-built confocal setup. The samples were imaged using an inverted Zeiss microscope with a 100× objective (NA of 0.85), and the light was focused on the entrance port of a triple grating Princeton Instrument imaging spectrophotometer (Acton SpectraPro SP-2500 equipped with a PIX100B-SF camera). An He—Ne laser was used as the excitation source at $\lambda_{Exc}$=632.8 nm, and the Rayleigh scattering was filtered using a notch Raman filter. For samples on multiplexed nanopyramid substrates, individual pyramids containing molecules were focused and the image was formed in the Princeton imaging spectrophotometer. Using the tip image with the respective spectra, the Raman spectra from each tip were mapped. The FTIR spectra were acquired using a Nicolet 6700 IR spectrometer with a spectral resolution of 1 cm$^{-1}$. The spectrometer was modified to incorporate imaging of the nanopyramids using an IR aspherical lens with antireflection coating for 8-12 μm (C028TME-F-f=5.95 mm, NA=0.56, Thorlabs).

Base Calling Algorithms for Optical Sequencing:

Identifying unknown k-mer blocks from Raman (and coupled FTIR) spectra requires comparing measurements on unknown k-mers to established fingerprints for known nucleobases. For the optical vibrational spectroscopic methods here, identifications are made via comparing characteristic fingerprint peaks, by calculating the area under the spectral curves. To establish fingerprints, OriginPro 2016 was used for fitting Gaussian curves to block k-mer spectra from homologous sequences (via the Fit Peaks functionality within the Peak Analyzer toolkit). From the Gaussians, the center location and corresponding full width at half maximum (FWHM) were determined for each characteristic peak in the spectra. Gaussian fitting was performed on five Raman spectra and one FTIR spectrum from homologous oligomers of each nucleobase (A, T, G, and C). The average peak center locations and FWHM from these spectra provided the fingerprints used for base calling.

The base calling analysis was implemented in MATLAB. The algorithm which is derived for characterizing unknown spectra operates by quantifying area under the curve within the FWHM region of known peak locations, or the fingerprints, for nucleobases A, T, G, and C. For identifying which nucleobases are present in a specific k-mer, a subset of spectra peaks for each nucleobase were considered (the peaks most unique for each nucleobase or those most often appearing together, as seen in FIG. 3, Panel a). Base calls are made for whichever nucleobases show the largest intensity (largest integrated area) in the unknown spectra. For homologous sequences, this can be quantified into a probability value for nucleobase i: $P_i = (\Sigma_{j=1}^{n}, A_{i,j}/F_{i,j})/n$ In this expression, n is the number of peaks used as fingerprints for identification, $A_{i,j}$ is the area under the curve within the FWHM region of peak j for nucleobase i, and $F_{i,j}$ is the FWHM of peak j for nucleobase i. $P_i$ values are normalized to the sum of probabilities for each nucleobase ($P_A + P_T + P_G + P_C$), and a single nucleobase can be called. For mixed sequences, this probability value is not used. Nucleobases are called if significant intensity is seen for characteristic fingerprint peaks, and their relative fraction is determined from correlations comparing measured intensity to known fractions (as seen in FIG. 3, Panels b and c).

While multiple embodiments are disclosed, still other embodiments of the present invention will become apparent to those skilled in the art from the following detailed description. As will be apparent, the invention is capable of modifications in various obvious aspects, all without departing from the spirit and scope of the present invention. Accordingly, the detailed description is to be regarded as illustrative in nature and not restrictive.

REFERENCES

Branton, D., et al., *Nat. Biotechnol.* 2008, 26, 1146.
Pozzi, E. A., et al., *ACS Nano* 2013, 7, 885.
Van Dijk, E. L., et al., *Trends Genet.* 2014, 30, 418.
Goodwin, S., et al., *Nat. Rev. Genet.* 2016, 17, 333.
Copeland, R. A., et al., *Oncogene* 2013, 32, 939.
P. Jares, D. Colomer, E. Campo, *Nat. Rev. Cancer* 2007, 7, 750.
Gire, S. K. et al., *Science* 2014, 345, 1369.
P. W. Laird, *Nat. Rev. Cancer* 2003, 3, 253.
Deng, J. et al., Nat. Biotechnol. 2009, 27, 353.
E. Bailo, V. Deckert, Angew. Chem., Int. Ed. 2008, 47, 1658.
A. Barhoumi, D. Zhang, F. Tam, N. J. Halas, J. Am. 2008, 130, 5523.
Guerrini, L., et al., Int. Ed. 2015, 127, 1160.
L. Xu, Z. Lei, J. Li, C. Zong, C. J. Yang, B. Ren, J. Am. Chem. Soc. 2015, 137, 5149.
Morla-Folch, J. et al., Angew. Chem., Int. Ed. 2015, 127, 13854.
S. Lal, N. K. Grady, J. Kundu, C. S. Levin, J. B. Lassiter, N. J. Halas, Chem. Soc. Rev. 2008, 37, 898.
K. Kneipp, Y. Wang, H. Kneipp, L. T. Perelman, I. Itzkan, R. R. Dasari, M. S. Feld, Phys. Rev. Lett. 1997, 78, 1667.
E. J. Blackie, E. C. Le Ru, P. G. Etchegoin, J. Am. Chem. Soc. 2009, 131, 14466.
K. Nakamoto, Handbook of Vibrational Spectroscopy, 2006.
D. Zhang, K. F. Domke, B. Pettinger, ChemPhysChem 2010, 11, 1662.
R. Treffer, R. Böhme, T. Deckert-Gaudig, K. Lau, S. Tiede, X. Lin, V. Deckert, Biochem. Soc. Trans. 2012, 40, 609.
S. Najjar, D. Talaga, L. Schue, Y. Coffinier, S. Szunerits, R. Boukherroub, L. Servant, V. Rodriguez, S. Bonhommeau, J. Phys. Chem. C 2014, 118, 1174.
N. C. Lindquist, P. Nagpal, A. Lesuffleur, D. J. Norris, S. H. Oh, Nano Lett. 2010, 10, 1369.
P. Nagpal, N. C. Lindquist, S.-H. Oh, D. J. Norris, Science 2009, 325, 594.
N. C. Lindquist, P. Nagpal, K. M. McPeak, D. J. Norris, S.-H. Oh, Rep. Prog. Phys. 2012, 75, 36501.
C. Ropers, C. C. Neacsu, T. Elsaesser, M. Albrecht, M. B. Raschke, C. Lienau, Nano Lett. 2007, 7, 2784.
A. Bouhelier, M. Beversluis, A. Hartschuh, L. Novotny, Phys. Rev. Lett. 2003, 90, 13903.
Q. C. Sun, H. Mundoor, J. C. Ribot, V. Singh, I. I. Smalyukh, P. Nagpal, Nano Lett. 2013, 14, 101.
N. A. Janunts, K. S. Baghdasaryan, K. V. Nerkararyan, B. Hecht, Opt. Commun. 2005, 253, 118.
M. Mathlouthi, A.-M. Seuvre, J. L. Koenig, Carbohydr. Res. 1984, 131, 1.
C. Otto, T. van den Tweel, F. de Mul, J. Greve, J. Raman Spectrosc. 1986, 17, 289.
J. De Gelder, K. De Gussem, P. Vandenabeele, L. Moens, J. Raman Spectrosc. 2007, 38, 1133.
R. Treffer, et al., Nanotechnol. 2011, 2, 628.
M. Mathlouthi, A.-M. Seuvre, J. L. Koenig, Carbohydr. Res. 1984, 134, 23.
M. Mathlouthi, A.-M. Seuvre, J. L. Koenig, Carbohydr. Res. 1986, 146, 1.
M. Mathlouthi, A.-M. Seuvre, J. L. Koenig, Carbohydr. Res. 1984, 146, 15.
A.-M. Seuvre, M. Mathlouthi, Carbohydr. Res. 1987, 169, 83.
A. Barhoumi, N. J. Halas, J. Phys. Chem. Lett. 2011, 2, 3118.
F. Pashaee, et al., Analyst 2016, 141, 3251.
S. Afsari, L. E. Korshoj, G. R. Abel Jr., S. Khan, A. Chatterjee, P. Nagpal, ACS Nano 2017.

All references disclosed herein, whether patent or non-patent, are hereby incorporated by reference as if each was included at its citation, in its entirety. In case of conflict between reference and specification, the present specification, including definitions, will control.

Although the present disclosure has been described with a certain degree of particularity, it is understood the disclosure has been made by way of example, and changes in detail or structure may be made without departing from the spirit of the disclosure as defined in the appended claims.

We claim:

1. A method for identification of nucleotide content in a portion of a polynucleotide, comprising:
   treating the polynucleotide to generate a polynucleotide fragment;
   applying the polynucleotide fragment to a surface;
   establishing a Ramen spectroscope and a Fourier transform infrared (FITR) spectroscope;
   directing a light source with a wavelength toward at least a portion of the polynucleotide fragment, wherein the portion comprises between 2 and 20 nucleotides;
   allowing the light to interact with the portion of the polynucleotide fragment;
   detecting light reflected by the portion of the polynucleotide fragment using said Ramen spectroscope and a Fourier transform infrared (FITR) spectroscope;
   determining an intensity of the Raman shift of the reflected light from about 200 to about 1500 cm-1;
   determining and amount of absorbance from about 600 to about 1800 cm-1;
   measuring the intensity of Raman shift at one or more wavenumbers between 200 and 1500 cm-1 and calculating an area under a curve for each measured wavenumber;
   determining the relative content of adenine, thymine, cytosine, and guanine in the portion based on the relative intensity of the one or more wavenumbers; thereby
   identifying the nucleotide content in the portion of the polynucleotide fragment.

2. The method of claim 1, further including the step of measuring the absorbance at one or more wavenumbers between 600 and 1800 cm-1 and calculating an area under the curve for each measured wavenumber to identify the relative content of adenine, thymine, cytosine, and guanine in the portion of the polynucleotide fragment.

3. The method of claim 2, wherein the Raman shift measurements are combined with the absorbance measurements to determine the content of the portion of the polynucleotide fragment.

4. The method of claim 3, wherein the one or more wavenumbers for measuring Raman shift are selected from the following Raman spectroscopy peaks:

TABLE 1

Raman spectroscopy peaks

| Peak | Shift (cm$^{-1}$) | Assignment |
|---|---|---|
| $A_1$ | 340 | Hydrogen bonding |
| $A_2$ | 537 | C—C=C bend |
| $A_3$ | 622 | N—C—C bend |
| $A_4$ | 737 | C—C and C—N in-phase stretch |
| $A_5$ | 971 | N—C=N bend |
| $A_6$ | 1045 | C—N—C bend |
| $A_7$ | 1140 | C2—N1=C6 bend |
|  |  | C5—N7=C8 stretch |
| $A_8$ | 1320 | C—N stretch |
| $A_9$ | 1350 | C=N stretch |
| $a_1$ | 841 | skeletal mode, in-plane |
| $a_2$ | 1167 | CH bend, in-plane |
| $T_1$ | 304 | OH . . . O bend |
| $T_2$ | 467 | N—C=C bend |
| $T_3$ | 647 | N—C—C bend |
| $T_4$ | 737 | C5—CH$_3$ stretch |
| $T_5$ | 832 | C4—C5 stretch |
| $T_6$ | 1017 | C—N—C bend |
| $T_7$ | 1059 | N—C—H bend |
| $t_1$ | 589 | C—C=C bend |
| $t_2$ | 953 | C5—C—H bend |
| $C_1$ | 395 | N3—C2=O and N1—C2=O bend |
| $C_2$ | 468 | C2—N1—C6 and N3=C4—C5 bend |
| $C_4$ | 538 | C—C=C and N3=C4—N4 bend |
| $C_5$ | 558 | C2—N3=C4 and N1—C2—N3 bend |
| $C_6$ | 611 | C=O in-phase stretch |
| $C_8$ | 788 | Breathing mode |
| $C_{10}$ | 973 | C4—C5 stretch |
| $c_2$ | 715 | C5—C4—N4 bend |
| $c_3$ | 1000 | C4—C5—H in-plane bend |
| $c_4$ | 1028 | N1—C6—H in-plane bend |
| $G_1$ | 402 | C=O bend |
| $G_2$ | 511 | N9—C4=C5 and N7—C=C4 bend |
| $G_3$ | 604 | C=C=C bend |
| $G_4$ | 648 | Breathing mode |
| $G_6$ | 847 | C—C stretch |
| $G_7$ | 931 | N—C=N and N—C—N bend |
| $G_{11}$ | 1226 | C$_2$—NH$_2$ stretch |
| $g_1$ | 548 | N3—C4=C5 bend |
| $g_3$ | 866 | N9—H out-of-plane bend. |

5. The method of claim 4, wherein the one or more wavenumbers for measuring absorbance are selected from the following FTIR spectroscopy peaks:

TABLE 2

| Peak | Wavenumber (cm$^{-1}$) | Assignment |
|---|---|---|
| $\alpha_2$ | 727 | C—C and C—N in-phase bend |
| $\alpha_3$ | 807 | C—C stretch |
| $\alpha_4$ | 869 | N9—H out-of-plane bend |
| $\alpha_5$ | 952 | N—C=N bend |
| $\alpha_7$ | 1129 | C2—N1=C6 bend |
|  |  | C5—N7=C8 stretch |
| $\alpha_9$ | 1371 | C2—H and C8—H out-of-plane bend |
|  |  | N=C—H bend |
| $\alpha_{10}$ | 1460 | Imidazole ring stretch |
| $\alpha_{11}$ | 1507 | C—N9—H bend |
| $\alpha_{12}$ | 1620 | C=N and C=C stretch |
| $\alpha_{13}$ | 1650 | NH$_2$ bend |
| $\tau_2$ | 861 | N—H out-of-plane bend |
| $\tau_7$ | 1227 | C—N stretch |
| $\tau_9$ | 1511 | N1—H and N3—H bend |
| $\tau_{12}$ | 1750 | C4=O and C2=O stretch |
| $\chi_1$ | 813 | N—H out-of-plane bend |
| $\chi_3$ | 1077 | NH$_2$ rocking |
| $\chi_4$ | 1235 | C4—N4 stretch |
| $\chi_5$ | 1361 | C=C—H bend |
| $\chi_6$ | 1458 | C4=N3 and C2—N3 stretch |
| $\chi_7$ | 1519 | C4=N3 and C4—N4 stretch |
| $\chi_8$ | 1626 | C5=C6 stretch |
| $\chi_9$ | 1708 | NH$_2$ bend |

TABLE 2-continued

| Peak | Wavenumber (cm$^{-1}$) | Assignment |
|---|---|---|
| $\gamma_2$ | 712 | Ring bend |
| $\gamma_3$ | 804 | Ni—H bend |
| $\gamma_4$ | 860 | C—C stretch |
| $\gamma_6$ | 1056 | NH$_2$ rocking |
| $\gamma_{10}$ | 1493 | N7=C8 and C8—C9 stretch |
| $\gamma_{12}$ | 1660 | C=O stretch |
| $\gamma_{13}$ | 1698 | C=O stretch |
|  |  | NH$_2$ bend. |

6. The method of claim 3, wherein the wavelength of light from the light source is about 632.8 nm.

7. The method of claim 6, wherein the light is passed through one or more filters before collecting.

8. The method of claim 3, wherein the surface is a plurality of probe tips.

9. The method of claim 8, wherein the nucleotide content of a plurality of portions of the polynucleotide are identified simultaneously from the plurality of probe tips.

10. The method of claim 1, wherein the polynucleotide on the surface is combed.

\* \* \* \* \*

SEQUENCE LISTING

<160> NUMBER OF SEQ ID NOS: 21

<210> SEQ ID NO 1
<211> LENGTH: 10
<212> TYPE: DNA
<213> ORGANISM: Artificial Sequence
<220> FEATURE:
<223> OTHER INFORMATION: Synthetic -continued

```
<400> SEQUENCE: 1
aaaaaaaaaa                                                                 10

<210> SEQ ID NO 2
<211> LENGTH: 10
<212> TYPE: DNA
<213> ORGANISM: Artificial Sequence
<220> FEATURE:
<223> OTHER INFORMATION: Synthetic

<400> SEQUENCE: 2
atgagtattc                                                                 10

<210> SEQ ID NO 3
<211> LENGTH: 10
<212> TYPE: DNA
<213> ORGANISM: Artificial Sequence
<220> FEATURE:
<223> OTHER INFORMATION: Synthetic

<400> SEQUENCE: 3
aacatttccg                                                                 10

<210> SEQ ID NO 4
<211> LENGTH: 10
<212> TYPE: DNA
<213> ORGANISM: Artificial Sequence
<220> FEATURE:
<223> OTHER INFORMATION: Synthetic

<400> SEQUENCE: 4
tgtcgccctt                                                                 10

<210> SEQ ID NO 5
<211> LENGTH: 10
<212> TYPE: DNA
<213> ORGANISM: Artificial Sequence
<220> FEATURE:
<223> OTHER INFORMATION: Synthetic

<400> SEQUENCE: 5
attccctttt                                                                 10

<210> SEQ ID NO 6
<211> LENGTH: 10
<212> TYPE: DNA
<213> ORGANISM: Artificial Sequence
<220> FEATURE:
<223> OTHER INFORMATION: Synthetic

<400> SEQUENCE: 6
ttgcggcatt                                                                 10

<210> SEQ ID NO 7
<211> LENGTH: 10
<212> TYPE: DNA
<213> ORGANISM: Artificial Sequence
<220> FEATURE:
<223> OTHER INFORMATION: Synthetic

<400> SEQUENCE: 7
ttgccttcct                                                                 10

<210> SEQ ID NO 8
```

```
<211> LENGTH: 10
<212> TYPE: DNA
<213> ORGANISM: Artificial Sequence
<220> FEATURE:
<223> OTHER INFORMATION: Synthetic

<400> SEQUENCE: 8
gtttttgctc                                                              10

<210> SEQ ID NO 9
<211> LENGTH: 10
<212> TYPE: DNA
<213> ORGANISM: Artificial Sequence
<220> FEATURE:
<223> OTHER INFORMATION: Synthetic

<400> SEQUENCE: 9
acccagaaac                                                              10

<210> SEQ ID NO 10
<211> LENGTH: 10
<212> TYPE: DNA
<213> ORGANISM: Artificial Sequence
<220> FEATURE:
<223> OTHER INFORMATION: Synthetic

<400> SEQUENCE: 10
gctggtgaaa                                                              10

<210> SEQ ID NO 11
<211> LENGTH: 10
<212> TYPE: DNA
<213> ORGANISM: Artificial Sequence
<220> FEATURE:
<223> OTHER INFORMATION: Synthetic

<400> SEQUENCE: 11
gtaaaagatg                                                              10

<210> SEQ ID NO 12
<211> LENGTH: 97
<212> TYPE: DNA
<213> ORGANISM: Artificial Sequence
<220> FEATURE:
<223> OTHER INFORMATION: Synthetic

<400> SEQUENCE: 12
cgccttcgtc ctatcggatc ataaggcggg aagccgacga tatatttcgg cgagttgctg      60
caagccacat caaggtttgg ctggaggaca ttgacta                                97

<210> SEQ ID NO 13
<211> LENGTH: 97
<212> TYPE: DNA
<213> ORGANISM: Artificial Sequence
<220> FEATURE:
<223> OTHER INFORMATION: Synthetic

<400> SEQUENCE: 13
ctcctggtcg acgtgcggaa cacgcccctc cttagacatt ggtaccaata accgtttcca      60
ccttgaccac tcgaccggcg ggattgtttt cagtcat                                97

<210> SEQ ID NO 14
<211> LENGTH: 98
<212> TYPE: DNA
<213> ORGANISM: Artificial Sequence
```

<220> FEATURE:
<223> OTHER INFORMATION: Synthetic

<400> SEQUENCE: 14
gtaactacgg aaatccccca atgagggaaa aacgattgtt ttggtctatt gcacgactgg    60
ctccttatta ttgtggcgga gattacggtt acccctga                           98

<210> SEQ ID NO 15
<211> LENGTH: 97
<212> TYPE: DNA
<213> ORGANISM: Artificial Sequence
<220> FEATURE:
<223> OTHER INFORMATION: Synthetic

<400> SEQUENCE: 15
gagaccacta gtcatgtgac aatataatag gaaaaataca tccgtatatc aaactgtcgg    60
tttgacgcta tctctatatt ctgttccgct tagacca                            97

<210> SEQ ID NO 16
<211> LENGTH: 97
<212> TYPE: DNA
<213> ORGANISM: Artificial Sequence
<220> FEATURE:
<223> OTHER INFORMATION: Synthetic

<400> SEQUENCE: 16
cgccttcgtc cgatcggatc ataaggcgtg aagccgacga tatatttcgg cgagttgctg    60
caagccacat caaggtttgg ctggatgaca gtgacta                            97

<210> SEQ ID NO 17
<211> LENGTH: 97
<212> TYPE: DNA
<213> ORGANISM: Artificial Sequence
<220> FEATURE:
<223> OTHER INFORMATION: Synthetic

<400> SEQUENCE: 17
ctcctggtcg acgtgcggaa cacgcccctc cttagacatg ggtaccaata accgtttcca    60
ccttgaccac tcgaccggcg ggagtggttt caggcat                            97

<210> SEQ ID NO 18
<211> LENGTH: 97
<212> TYPE: DNA
<213> ORGANISM: Artificial Sequence
<220> FEATURE:
<223> OTHER INFORMATION: Synthetic

<400> SEQUENCE: 18
taactacgga aagcccccaa tgagggaaaa acgattgttt gggtctattg cacgactggc    60
gccttattat tgtggcggag attacgggta cccctga                            97

<210> SEQ ID NO 19
<211> LENGTH: 97
<212> TYPE: DNA
<213> ORGANISM: Artificial Sequence
<220> FEATURE:
<223> OTHER INFORMATION: Synthetic

<400> SEQUENCE: 19
tagaccacta gtcatgtgac aatataatag gaaaaataca tccgtatatc aaactgtcgg    60
tttgactcga tctctatatt ctgttccgct tagacca                            97

<210> SEQ ID NO 20
<211> LENGTH: 27
<212> TYPE: DNA
<213> ORGANISM: Artificial Sequence
<220> FEATURE:
<223> OTHER INFORMATION: Synthetic

<400> SEQUENCE: 20
acgctatctc tatattctgt tccgctt                                            27

<210> SEQ ID NO 21
<211> LENGTH: 27
<212> TYPE: DNA
<213> ORGANISM: Artificial Sequence
<220> FEATURE:
<223> OTHER INFORMATION: Synthetic

<400> SEQUENCE: 21
actcgatctc tatattctgt tccgctt                                            27